(12) United States Patent
Gutheil

(10) Patent No.: US 7,786,259 B2
(45) Date of Patent: Aug. 31, 2010

(54) ATTACHMENT AND ELABORATION STRATEGIES FOR INVERSE PEPTIDE SYNTHESIS

(75) Inventor: William G. Gutheil, Kansas City, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 11/777,899

(22) Filed: Jul. 13, 2007

(65) Prior Publication Data

US 2008/0039612 A1    Feb. 14, 2008

Related U.S. Application Data

(60) Division of application No. 10/848,964, filed on May 19, 2004, now Pat. No. 7,244,815, which is a continuation-in-part of application No. 10/156,669, filed on May 23, 2002, now Pat. No. 7,214,769.

(60) Provisional application No. 60/293,273, filed on May 23, 2001.

(51) Int. Cl.
C07K 1/04    (2006.01)
(52) U.S. Cl. .................. 530/334; 530/333; 530/335
(58) Field of Classification Search ............. 530/333, 530/334, 335
See application file for complete search history.

(56) References Cited

U.S. PATENT DOCUMENTS 7,214,769 B2 * 5/2007 Gutheil et al. ............ 530/333
2008/0200644 A1    8/2008 Gutheil et al.

FOREIGN PATENT DOCUMENTS

WO    WO-90/05738    5/1990
WO    WO-93/05065    3/1993

OTHER PUBLICATIONS

Matseuda (J. Am. Chem Soc. 97, 2573-75, 1975).*
Maruyama, Hiroshi (Bulletin of the Chemical Society of Japan 49(8), 2259-67, 1976).*
"U.S. Appl. No. 11/789,494, Non-Final Office Action mailed Mar. 30, 2009", 13 pgs.
Felix, A. M, et al., "Azide Solid Phase Peptide Synthesis", *J. Am. Chem Soc.* vol. 92, (1970), 1385-91.
Johansson, A., et al., "An Improved Procedure for N- to C- Directed (Inverse) Solid-Phase Peptide Synthesis", *J.Comb. Chem.*, 2000 vol. 2 (5), http://pubs.acs.org, (Aug. 9, 2000), 496-507 pgs.
U.S. Appl. No. 10/156,669 Final Office Action mailed Sep. 15, 2006, 5 pgs.
U.S. Appl. No. 10/156,669 Non-Final Office Action mailed Mar. 18, 2005, 9 pgs.
U.S. Appl. No. 10/156,669 Non-Final Office Action mailed Apr. 10, 2006, 5 pgs.
U.S. Appl. No. 10/156,669 Non-Final Office Action mailed Sep. 1, 2005, 6 pgs.
U.S. Appl. No. 10/156,669 Notice of Allowance mailed Dec. 26, 2006, 4 pgs.
U.S. Appl. No. 10/156,669 Response filed Nov. 16, 2006 to Final Office Action, 9 pgs.
U.S. Appl. No. 10/156,669 Response filed Feb. 28, 2006 to Non-Final Office Action, 11 pgs.
U.S. Appl. No. 10/156,669 Response filed Jun. 20, 2005 to Non-Final Office Action, 10 pgs.
U.S. Appl. No. 10/156,669 Response filed Jul. 10, 2006 to Non-Final Office Action, 13 pgs.
U.S. Appl. No. 10/848,964 Advisory Action mailed Dec. 19, 2006, 5 pgs.
U.S. Appl. No. 10/848,964 Amendment and Response under 37 CFR 1.116 filed Feb. 15, 2007, 14 pgs.
U.S. Appl. No. 10/848,964 Final Office Action mailed Sep. 15, 2006, 6 pgs.
U.S. Appl. No. 10/848,964 Non-Final Office Action mailed Apr. 10, 2006, 7 pgs.
U.S. Appl. No. 10/848,964 Notice of Allowance mailed Mar. 13, 2007, 4 pgs.
U.S. Appl. No. 10/848,964 Response filed Jul. 10, 2006 to Non-Final Office Action mailed Apr. 10, 2006, 15 pgs.
U.S. Appl. No. 10/848,964 Response filed Nov. 16, 2006 to Final Office Action mailed Sep. 15, 2006, 15 pgs.
Gutheil, William G., et al., "N-to-C Solid-Phase Peptide and Peptide Tirflouromethylketone Synthesis Using Amino Acid tert-Butyl Esters", *Chem. Pharm. Bull.* 50(5), (Feb. 20, 2002), 688-691.
Maruyama, H. , et al., "Solid Phase Peptide Synthesis by Oxidation-Reduction Condensation. Synthesis of Adrenocorticotropin(1-24)by Chain Elongation at the Carboxyl End on Solid Support", *Bulletin of the Chemical Society of Japan*, 49 (8), (1976), 2259-2267.

(Continued)

*Primary Examiner*—David Lukton
(74) *Attorney, Agent, or Firm*—Schwegman, Lundberg & Woessner, P.A.

(57) ABSTRACT

The present invention provides a process for preparing an immobilized peptide derivative of formula (Vb):

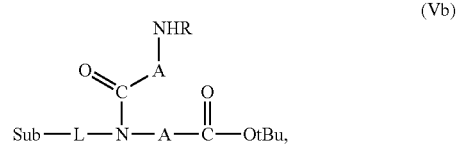

comprising reacting a functionalized solid support comprising Sub-L wherein Sub is a solid support and L is a cleavable linker, with H—[NH—A—C(O)]—O(tBu), then reacting the immobilized product with compound of the formula RHN—A—C(O)OH, wherein the RHN—A—C(O) group is the residue of a N-protected α-amino acid, in the presence of a coupling agent, to yield an immobilized peptide derivative of the formula (Vb).

36 Claims, 9 Drawing Sheets

OTHER PUBLICATIONS

Matsueda, Rei, et al., "Solid phase peptide synthesis by oxidation-reduction condensation.", *Journal of the American Chemical Society*, 97(9), (Apr. 30, 1975), 2573-75.

Matsueda, Rei, "Solid Phase Peptide Synthesis by Oxidation-Reduction Condensation. Synthesis of LH-RH by Fragment Condensation on Solid Support", *Bulletin of the Chemical Society of Japan*, vol. 46, No. 10, (1973), 3240-3247.

Rai, Aman, et al., "A Dde Resin Based Strategy for Inverse Solid-Phase Synthesis of Amino Terminated Peptides, Peptide Mimetics and Protected Peptide Intermediates", *Journal of Peptide Science*, (2004) 5 pgs.

Sasubilli, Ramakrishna, et al., "General Inverse Solid-Phase Synthesis Method for C-Terminally Modified Peptide Mimetics", *J. Comb. Chem.*, 6, (2004), 911-915.

Xu, Qingchai, et al., "A New Strategy for Inverse Solid-Phase Peptide Synthesis", *Peptides: The Wave of the Future; American Peptide Society*, 2001, (2001), 234-235.

* cited by examiner (a) 50% TFA/DCM; (b) HATU/TMP, 5 eq of AA-OtBu•HCl; (c) TFMSA/TFA.

(a) HATU/TMP, 5 eq of DL-boroAla-pinacol (HCl salt) in DMF for Eh; (b) 10% TFMSA/TFA, 2h.

(a) HATU/TMP, 5 eq of NH₂CH(CH₃)CH(OH)CF₃, in DMF for 4h; (b) 10 eq DCC/ 1 eq CHCl₂COOH/100 μL DMSO/100 μL toluene, 18h, repeat once; (c) 10% TFMSA/TFA, 2h.

(a) HATU/TMP, 5 eq of *O*-(*t*-butyl)hydroxylamine hydrochloride in DMF FOR 4h; (b) 10% TFMSA/TFA, 2h.

(a) HATU/TMP, NH₂CH(CH₃)CH(OH)CF₃, in DMF for 6h, then repeat once;
(b) DCC/CHCl₂COOH/DMSO/toluene (10 eq/1 eq/0.2 ml/0.2 ml) 18h, and then repeat once;
(c) 5% v/v hydrazine/DCM

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: A synthetic peptide beginning with Suc

<400> SEQUENCE: 1

Ala Leu Pro Phe
 1

<210> SEQ ID NO 2
<211> LENGTH: 4
<212> TYPE: PRT
<213> ORGANISM: Artificial Sequence
<220> FEATURE:
<223> OTHER INFORMATION: A synthetic peptide
```

```
<220> FEATURE:
<221> NAME/KEY: SITE
<222> LOCATION: 4
<223> OTHER INFORMATION: Xaa = boronated Ala

<400> SEQUENCE: 2

Asn Leu Glu Xaa
 1

<210> SEQ ID NO 3
<211> LENGTH: 4
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 4
<223> OTHER INFORMATION: Xaa = boronated Ala

<400> SEQUENCE: 3

Phe Ala Gly Xaa
 1

<210> SEQ ID NO 4
<211> LENGTH: 4
<212> TYPE: PRT
<213> ORGANISM: Artificial Sequence
<220> FEATURE:
<223> OTHER INFORMATION: A synthetic peptide ending in CH(OCH2)2 or
      CH2OH([M+H] = 486.6)

<400> SEQUENCE: 4

Gln Phe Lys Ala
 1

<210> SEQ ID NO 5
<211> LENGTH: 4
<212> TYPE: PRT
<213> ORGANISM: Artificial Sequence
<220> FEATURE:
<223> OTHER INFORMATION: A synthetic peptide ending (Z)-OtBu or OH

<400> SEQUENCE: 5

Tyr Ala Val Lys
 1
```

ATTACHMENT AND ELABORATION STRATEGIES FOR INVERSE PEPTIDE SYNTHESIS

CROSS-REFERENCE TO RELATED APPLICATIONS

This application is a divisional of U.S. patent application Ser. No. 10/848,964, filed May 19, 2004, now U.S. Pat. No. 7,244,815, which is a continuation-in-part of U.S. patent application Ser. No. 10/156,669, filed May 23, 2002, now U.S. Pat. No. 7,214,769, which claims priority of U.S. provisional application Ser. No. 60/293,273, filed May 23, 2001. These applications are incorporated herein by reference.

STATEMENT OF GOVERNMENT RIGHTS

This invention was made with support of the National Institutes of Health under Grant No. GM60149. The U.S. Government has certain rights in this invention.

BACKGROUND OF THE INVENTION

The standard methods for the solid phase synthesis of peptides (SPPS) on beaded resins in the normal C-to-N direction are well developed, as they must be if long peptides are to be synthesized (reviewed in M. Bodanszky et al., "Peptide Chemistry: A Practical Textbook," Springer-Verlag, NY (2d ed., 1993) and M. Bodanszky et al., "The Practice of Peptide Synthesis," Springer-Verlag, NY (2d ed., 1993) S. A. Kates et al., Solid-phase peptide synthesis: a practical guide. Marcel Dekker, New York (2000)). These methods are based on attaching the carboxy terminus of an amino-protected amino acid to the resin. The amino protecting group is then selectively removed. A suitably amino-protected amino acid is coupled to the resin attached nascent peptide with a suitable coupling strategy, and the amino-protecting group of the newly attached residue is removed to complete the cycle. This process is repeated until the desired peptide sequence and length is completed, and the product peptide is then cleaved from the resin, and amino acid side chain protecting groups removed using suitable methods well known in the art. Suitable amino protecting groups in common usage include Boc and Fmoc protecting groups.

Standard peptide chemistry has served as a basis for the development of combinatorial methods for the solid phase synthesis of peptide libraries of tremendous diversity (H. M. Geysen et al., *Molec. Immunol.*, 23, 709 (1986); R. A. Houghten et al., *Nature*, 354, 84 (1991); K. S. Lam et al., *Nature*, 354, 84 (1991); reviewed in J. Ellman et al., "Combinatorial thinking in chemistry and biology" *Proc. Natl. Acad. Sci. USA*, 94, 2779 (1997); R. A. Houghten, "Parallel array and mixture-based synthetic combinatorial chemistry: tools for the next millennium" *Annu. Rev. Pharmacol. Toxicol.*, 40, 273 (2000); K. S. Lam, et al., "Applications of one-bead one-compound combinatorial libraries and chemical microarrays in signal transduction research," *Acc. Chem. Res.*, 36, 370 (2003)). Combinatorial methods are now widely used for drug and bioactive agent discovery.

Peptide mimetics are agents closely related to peptides but with key functional group modifications tailored for specific properties and applications. Peptide mimetics are of high interest as bioactive agents and drugs, and a number of drugs and bioactive agents in current use are peptide mimetics, including ACE inhibitors (M. Harrold et al., in Foye's principles of medicinal chemistry, D. A. Williams et al., eds., Lippincott, Philadelphia (2002) at pages 533-588), HIV protease inhibitors (M. L. Sethi et al., *op. cit.*, at 952-979), and the anti-myeloma agent Velcade (J. Adams, *Drug Disc. Today*, 8, 307 (2003)). Many biological processes can conceivably be targeted through suitably designed peptide mimetics, and the development of general solid-phase approaches to such agents is expected to greatly facilitate efforts to develop and refine peptide mimetics for specific applications.

Peptide mimetic combinatorial libraries, based on the normal C-to-N direction of peptide synthesis, have been described. A peptide phosphinate library has been synthesized and used to find potent and selective inhibitors of zinc metalloproteases (J. Jiracek et al., *J. Biol. Chem.*, 270, 21701 (1995); J. Jiracek et al., *J. Biol. Chem.*, 271, 19606 (1996); V. Dive et al., *PNAS USA*, 96, 4330 (1999)). A (hydroxyethyl)amine library has also been synthesized and used to find inhibitors of the prototypical aspartyl protease Cathepsin D (E. R. Kick et al., *Chem. Biol.*, 4, 297 (1997)).

Many peptide mimetic classes of interest as drugs and bioactive agents are modified on the C-terminus, or are derived from carboxyl group reactions. Simple C-terminal peptide mimetics include peptide trifluoromethylketones (M. H. Gelb et al., *Biiochemistry*, 12, 1813 (1985); D. Rasnick, *Anal. Biochem.*, 149, 461 (1985); B. Imperiali et al., *Tetrahedron Lett.*, 27, 135 (1986)); peptide boronic acids (D. S. Matteson et al., *J. Amer. Chem. Soc.*, 103, 5241 (1981); C. A. Kettner et al., *J. Biol. Chem.*, 259, 106 (1984); W. W. Bachovchin et al., *Biochemistry*, 27, 7689 (1988); M. P. Groziak *Am. J. Ther* 8, 321 (2001)); peptide hydroxamic acids (W. Zhang et al., *J. Carb. Chem.* 3, 151 (2001)); peptide alcohols (D. S. Cafiso, *Annu. Rev. Biophys. Biomol. Struct* 23, 141 (1994); J. K. Chugh et al., *Biochem. Soc. Trans* 29, 565 (2001)); and peptide aldehydes (H. T. Morishima, et al., *J. Antibiot.* (Tokyo), 23, 263 (1970); H. T. Umezawa et al., op. cit., at 259-62 (1970); R. C. Thompson, *Biochemistry*, 12, 47 (1973); K. L. Rock et al., *Cell* 78, 761 (1994); D. Banerjee et al., *Anticancer Res.*, 21 (6A), 3941 (2001)). Peptide mimetic classes which are accessible through carboxyl group chemistry include statine homologs (J. Marciniszyn, et al., *Adv. Exp. Med. Biol.*, 95, 199 (1977); K. E. Rittle et al., *J. Org. Chem.* 47, 3016 (1982); M. H. Gelb et al., *Biochemistry*, 24, 8, 1813 (1985); J. A. Fehrentz et al., *Biochem. Biophys. Res. Comm.*, 188, 873 (1992); J. A. Fehrentz op. cit., at 865; J. M. Travins et al., *Org. Lett.*, 3, 2725 (2001); R. K. Hom et al., *J. Med. Chem.* 47, 158 (2004)); and hydroxyethylene isosteres (G. B. Dreyer et al., *Biochemistry*, 31, 6646 (1992); J. J. Konvalinka et al., *Eur. J. Biochem.*, 250, 559 (1997); M. S. Shearman et al., *Biochemistry*, 39, 8698 (2000); Hom et al., cited above).

Given the interest in these peptide mimetic classes, a number of approaches to C-terminally modified peptide mimetics have been described (J. Alsina et al., *Biopolymers*, 71, 454 (2003)). These approaches can be divided into several sub-categories, including 1) attachment through the C-terminal functional group or precursor followed by standard C-to-N peptide synthesis, 2) attachment through the backbone followed by C-to-N peptide synthesis, and 3) attachment through the amino terminus followed by N-to-C (inverse) peptide synthesis (inverse solid phase peptide synthesis; ISPPS).

The first of these general approaches, based on C-terminal functional group specific attachment strategies, are limited to a specific functional group and do not allow further elaboration of the final functional group to be made on the resin, for example, to prepare additional derivatives of a solid phase attached C-terminal functional group such as an aldehyde or chloromethylketone. The second general approach does allow further reaction of the final functional group, but suffers, as does the first approach, from the limitation that the peptide chain is synthesized in the C-to-N direction, away from the C-terminal functional group. For split-pool combinatorial peptide mimetic synthesis followed by iterative deconvolution to obtain optimized agents, which is arguably one of the better approaches to combinatorial optimization, it is the last residues added to a molecule which are optimized first (D. A. Konings et al., *J. Med. Chem.*, 40, 4386 (1997)). In both the first and second of the above cited general approaches these are the residues furthest away from the C-terminal functional group.

In contrast to the first two attachment approaches just discussed, the third approach based on ISPPS provides the C-terminus of the nascent peptide mimetic for elaboration into desired functional groups, and for further elaboration into further derivatives, and also allows the residues closest to the C-terminus to be optimized first when using split-pool/iterative deconvolution optimization strategy. There have been a number of efforts to develop effective ISPPS strategies. The first was suggested by R. L. Letsinger and M. J. Komet, *J. Amer. Chem. Soc.*, 85, 3045 (1963) using amino acid ethyl esters. Merrifield et al., *J. Amer. Chem. Soc.*, 92, 1384 (1970), used protected amino acid hydrazides as building blocks for the C-terminal elongation of peptides, followed by deprotection and subsequent reaction of the hydrazide function with nitrite, allowed the next building block to be coupled by the azide method. However, the procedure is elaborate, requiring activation and coupling at low temperature with moderate yields.

Sharma et al. have described a few C-terminally modified tetrapeptide HIV-1 protease inhibitors, generated in the inverse direction. For example, see R. P. Sharma et al., published PCT applications WO 93/05065 (18 Mar. 1993) and WO 90/05738 (31 May 1990) and *Chem. Commun.*, 1449 (1998). Sharma's approach relies on the coupling of amino acid tri-tert-butoxysilyl (Sil) esters. More recently, A. Johannsson et al., *J. Comb. Chem.*, 2, 496 (2000) described a modification of the method of Sharma et al. that involves the coupling of a photolabile resin-bound C-terminal amino acid with excess amounts of amino acid tri-tert-butoxysilyl (Sil) esters, using HATU as coupling reagent and 2,4,6-trimethylpyridine (TMP, collidine) as a base. The HATU/TMP coupling method gave levels of epimerization considerably lower than those reported for other N-to-C methods, usually a ca. 5% and occasionally even below 1%. Amino acid silyl esters are however not commercially available, and are difficult to prepare, unstable to store, and unstable under peptide coupling conditions.

Alternatively, amino acid 9-fluorenylmethyl (Fm) (B. Henkel et al., *Liebigs Annalen Recueil*, (10), 2161 (1997)), and amino acid allyl esters (N. F. Thieriet et al., *Org. Letters* 2, 1815 (2000)) have also been used for ISPPS. The Fm ester approach appears attractive considering its similarity to standard Fmoc based C-to-N SPPS, but Fm esters are not as stable as Fmoc amino acids, and Fm ester based inverse peptide synthesis apparently suffers from this limitation. The allyl ester based approach is practicable, but allyl esters are not generally available, and deprotection requires the use of 20 mol % of Pd(PPh$_3$)$_4$, which is a heavy metal based reagent. These strategies therefore appear less than ideal, since suitable amino acid derivatives are not generally available commercially and can be difficult to prepare, due to instability of reactants and intermediates, and to toxicity and expense of reagents.

Thus, a continuing need exists for simple and efficient methods for the inverse (N-to-C) synthesis of peptides and peptide mimetics, particularly for the synthesis of oligopeptide mimetic libraries useful for high-throughput drug screening.

SUMMARY OF THE INVENTION

The present invention provides a process for preparing a peptide of formula (I):

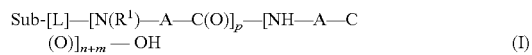

comprising (a) reacting an immobilized compound of formula (II):

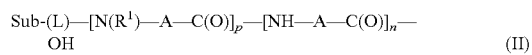

with an amino acid ester or peptide derivative of formula (III):

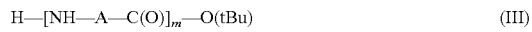

in the presence of a coupling agent to yield a peptide compound of general formula (IV):

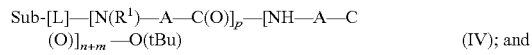

(b) removing the tBu (t-butyl) group to produce a solid-support bound carboxylic acid or peptide derivative of general formula (I);

wherein n is a positive integer, e.g., 1-10, preferably 1-5; m is a positive integer, e.g., 1-10, preferably 1-5; and p is 0 or 1. Sub is a solid support such as a polymer or glass substrate, preferably comprising free OH, or NH$_2$ groups. L is a linker to the amino acid ester or peptide derivative. R$^1$ is a removable amino-protecting group, such as RCH$_2$OC(O)—, or an irreversible N-capping group such as RSO$_2$—, RC(O)— or R—NHC(O)—, wherein R is an organic group, e.g., R—NH—(A)C(O). Each A independently is the residue of a naturally occurring or synthetic amino acid; a peptide residue, such as an oligopeptide or polypeptide; or the structure —NH-A represents a heterocyclic group, e.g., a C$_5$-C$_{10}$ heterocyclic group comprising 1-2 O, N and/or S such as pyrrolidine, indole or imidazole. This approach is summarized in FIG. 1, wherein p is 0, CHR represents the residue of an α-amino acid and O— represents Sub.

In one embodiment, the present method optionally comprises, prior to step (a): forming a solid-support bound compound of general formula (V):

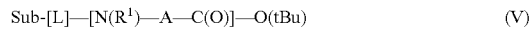

wherein (R$^1$) is as defined above, by (i) reacting a functionalized solid support of general formula Sub[L]X with a compound of formula: H—[NH—A—C(O)]—O(tBu), wherein X is a group such as CO$_2$H, —O(CO)Cl, —CHO, CH$_2$X, wherein X is a leaving group such as Cl, Br, I, OTs, OMs and the like, (R$^1$)(R$^2$)C═C(OH)—, wherein R$^1$ and R$^2$ together with the carbon atom to which they are attached form a 4,4-dimethyl-cyclohexyliden-1-yl-2,3-dione group, or an activated carboxylic acid ester, that links L to NH$_2$—A, e.g., by elimination of H$_2$O, HCl, and the like, and (ii) protecting or capping the secondary amino group thus formed to yield a compound of formula V:

wherein R$^1$ is as defined above. The t-Bu group can be then removed under conditions under which R$^1$ is retained to yield a compound of formula VI:

Compound VI can be reacted with H[HN—A—CO]$_n$(tBu) to yield a compound VII of formula:

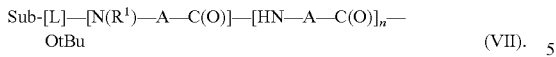

Alternatively, if $R^1$ is an N-protecting group, the N-protecting group $R^1$ of (V) can be removed and the secondary amino group (preferably —CH$_2$NH—A—) reacted with an activated, N-protected alpha-amino acid to yield (Va):

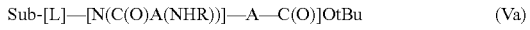

optionally followed by N-deprotection and further acylation to yield (VIII), comprising a C-to-N peptide or peptido mimetic chain (Pep),

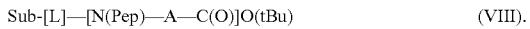

The terminal tBu group can then be removed and the inverse synthesis carried out to yield a compound of formula IV wherein $R^1$ has been elaborated. Preferred moieties [L]X include —OC(O)(CH$_2$)$_2$CH(NHZ)CO$_2$H, —HNC(O)(CH$_2$)$_2$ CH(NHZ)CO$_2$H, and C(O)(CH$_2$)$_2$CO$_2$H; particularly preferred [L]X include:

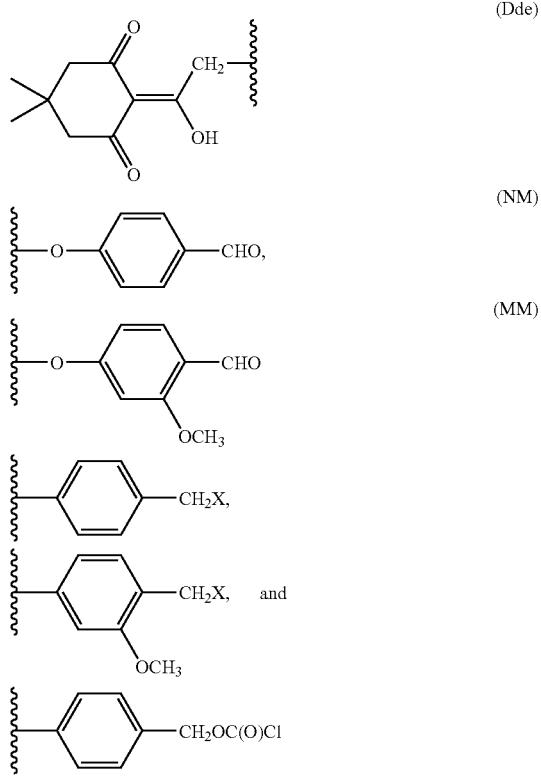

wherein X is a suitably-reactive leaving group such as halo, OMs, OTs and the like and Z is H or an amino protecting group such as benzyloxycarbonyl (Cbz).

The present method preferably further comprises the step of cleaving compound (IV) at the L-NH or L-N($R^1$) bond to yield a compound of formula (IX):

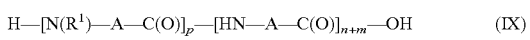

or of cleaving compound (IV) at the Sub-(L) bond to yield a compound of formula (X):

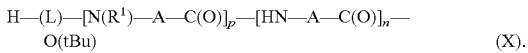

Side chain and carboxyl protecting groups can be removed concurrently with cleavage from the resin where cleavage is effected by TFMSA/TFA. In the case of the Dde attachment strategy, where the product peptides are cleaved from the resin with dilute hydrazine, side chain protecting groups are retained during cleavage, and can be removed subsequently with TFMSA/TFA treatment, as necessary. $R^1$ can be retained or removed to yield an N-terminal NH$_2$ group or an H-(L)-NH— group.

The present method preferably further comprises, the following step; carrying out, x times, the steps of reacting compound (I) with a compound of formula (III) and removing the tBu group to yield a compound of formula (XI):

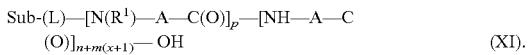

For example, p is 0 and if n and m are both 1, and A is an amino acid residue, carrying out the steps 3 times will yield an immobilized oligopeptide having 5 peptidyl residues, not including L. The values n+m (x+1) can be any integer up to the maximum number of residues yielding a useful polypeptide or polypeptide analog, e.g., about 75-100. Compound (VIII) can also be cleaved at the sub-(L) bond or the (L)-NH bond to yield compounds analogous to compounds (IX) and (X) above.

Novel compounds, particularly immobilized peptides, are also within the scope of the present invention, e.g., compounds (I), (II), (III), (IV), (VI), (VIa), (VII), (VIII), (IX), (X), (XI), and the like.

Preferably, each A is individually the residue of an c's-amino acid, most preferably, a residue of a naturally-occurring L-amino acid, such as the alkylidenyl or substituted alkylidenyl residues derived from glycine (Gly) (CH$_2$—), alanine (Ala) (CH$_3$CH—), seine (Ser) HOCH$_2$CH—), threonine (Thr) (CH$_3$CHOHCH—), valine (Val) (CH$_3$CH(CH$_3$)CH—), leucine (Leu) (—CH$_3$CH(CH$_3$)CH$_2$CH), isoleucine (Ile) (CH$_3$CH$_2$CH(CH$_3$)CH—), cysteine (CySH)(CH$_2$(SH)CH—), cystine (SyS—SCy)[—SCH$_2$CH—]$_2$, phenylalanine (Phe) (PhCH$_2$CH—), tyrosine (Tyr) (4-HOPhCH$_2$CH—), proline (Pro) (pyrrolidin-2-yl) with the exception that A in Sub-L—[NH—A—C(O)]OtBu cannot be Pro (pyrrolidin-2-yl); hydroxyproline (4-hydroxy-2-pyrrolidinyl), tryptophan (Trp) ((indol-3-yl)CH$_2$CH—), aspartic acid (Asp) (HOOCCH$_2$CH—), glutamic acid (HOOCCH$_2$CH$_2$CH—); histidine (His) ((imidazol-3-yl)(CH$_2$CH—), lysine (Lys) (H$_2$N—(CH$_2$)$_4$CH—), or arginine (Arg) (H$_2$NC(=NH)(CH$_2$)$_3$CH—). Side chains (A) in NH—A—C(O)— can be any common D or L amino acid, including Proline, as well as beta- and gamma-amino acids. Side chains in N($R^1$)—A—C(O) can be anything except Pro, hydroxyproline, or any other secondary amine based amino acids. Free CO$_2$H, NH$_2$, OH, or SH groups on A groups can optionally be protected with suitable protecting groups (Z or P) such as tBoc, Cbz, acyl, benzyl, silyl, Dde, hemiacetals, or alkyl.

The present method can also be readily adapted to form C-terminal modified peptides, for example, by reacting compound (I) or (XI) with H$_2$N(A)CH(OH)CF$_3$, such as H$_2$N(alkyl)CH(OH)CF$_3$, wherein alkyl is preferably (C$_1$-C$_6$)alkyl to yield the corresponding amide of (I) or (XI) and oxidizing the CH(OH) moiety to yield a trifluoromethyl ketone of general formula:

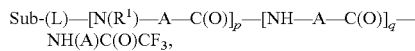
Sub-(L)—[N(R$^1$)—A—C(O)]$_p$—[NH—A—C(O)]$_q$—NH(A)C(O)CF$_3$, wherein p is 0 or 1, q is n+m or n+m(x+1), respectively, followed by cleaving the compound from Sub or Sub-(L) to yield a compound of formula:

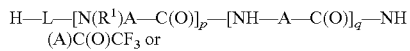
H—L—[N(R$^1$)A—C(O)]$_p$—[NH—A—C(O)]$_q$—NH(A)C(O)CF$_3$ or

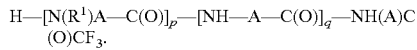
H—[N(R$^1$)A—C(O)]$_p$—[NH—A—C(O)]$_q$—NH(A)C(O)CF$_3$.

Compounds such as (I) or (XI) can also be reacted with H$_2$N—A—CH$_2$OR, where A is as above and R is H or a suitable OH protecting group, such as tBu or tetrahydropyran to yield the hydroxyalkylamide of (I) or (XI) and deprotecting and oxidizing the terminal hydroxyl group to yield a terminal aldehyde of formula:

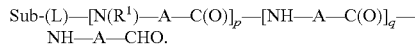
Sub-(L)—[N(R$^1$)—A—C(O)]$_p$—[NH—A—C(O)]$_q$—NH—A—CHO.

The terminal CHO group can be protected by conversion into an ethylene glycol acetal, a propylene glycol acetal, 2,3-dimethyl-2,3-butylene glycol acetal, an ethylene dithiol acetal or a 1,3-dithiane, and cleaved from the substrate to yield

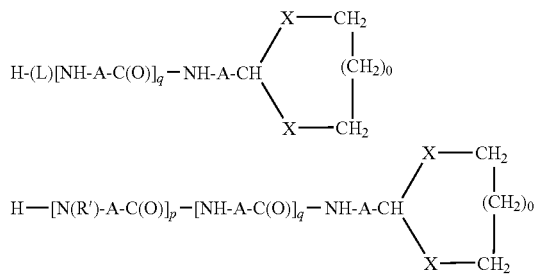

wherein X is O and/or S, and p is 0 or 1 and o is 0 or 1. The group A is as defined above or is preferably a (C$_1$-C$_6$)alkyl moiety, including the alkylidenyl or substituted alkylidenyl moieties described hereinabove.

Compound (I) or (IX) can also be reacted with a boroamine to yield peptide boronic acids of the general formula:

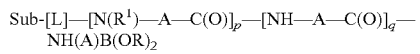
Sub-[L]—[N(R$^1$)—A—C(O)]$_p$—[NH—A—C(O)]$_q$—NH(A)B(OR)$_2$ wherein R is H, (C$_1$-C$_6$)alkyl, phenyl or the residue of an organic diol such as pinanediol, catechol, pinacol, diethanolamine and the like. See, Kettner (U.S. Pat. No. 4,499,082). R can be removed, if necessary, and the peptide can be cleaved from Sub to yield a compound of the formula:

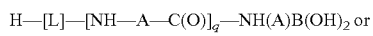
H—[L]—[NH—A—C(O)]$_q$—NH(A)B(OH)$_2$ or

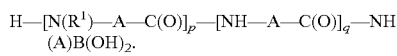
H—[N(R$^1$)—A—C(O)]$_p$—[NH—A—C(O)]$_q$—NH(A)B(OH)$_2$.

As noted above, in some cases, it is desirable to cleave the N—R$^1$ bond to generate a free terminal amino group.

The corresponding terminal chloromethyl ketone, C(O)CH$_2$Cl, can be prepared from the free CO$_2$H compounds as disclosed below.

In accord with the present method, reversing the direction of peptide synthesis provides the chemically versatile carboxy group for modification. This approach has significant advantages for preparing solid phase peptides with either a free carboxy terminus or a carboxy terminal peptide mimetic. These advantages include:

1) The ability to prepare immobilized peptides with free carboxy terminus;
2) The ability to prepare immobilized peptides with a directly modified carboxy terminus, for example, peptide esters, peptide amides, peptide aldehydes, and peptide chloromethyl ketones; and
3) The ability to introduce other monomer groups, such as amino acid mimetics such as boronic acid based amino acid analogs (boroamines) and trifluoromethyl ketones, onto the carboxy terminus.

Such derivatives, such as peptide aldehydes and chloromethyl ketones, can themselves serve as intermediates during the syntheses of other derivatives. For example, peptide chloromethyl ketones can be treated with nucleophilic reagents, which will displace the chloride ion, to make further derivatives. Aldehydes are also versatile synthetic intermediates amenable to a wide variety of additional elaboration reactions. This synthetic versatility of the carboxy group allows tremendous chemical diversity to be accessed via the inverse N-to-C peptide synthesis method described here.

As prepared in accord with the present method, peptide and peptide mimetic libraries can be screened for drug leads or for other desirable properties. The present invention can provide novel sets of peptide mimetic libraries for use in such screens. Most notably, this invention provides a way to generate chemical substances of particular interest for the discovery of potent and specific protease inhibitors, especially the serine and cysteine proteases. Many protease inhibitor classes are based on carboxy group chemistry. Examples include peptide boronic acids, peptide aldehydes, peptide chloromethyl ketones, peptide aldehydes and peptide fluoromethyl ketones. Further elaboration can be envisioned into additional inhibitor functional groups of interest, including extended peptide mimetics such statine homologs (J. Marciniszyn, Jr. et al., *Adv. Exp. Med. Biol.*, 95, 199 (1977); K. E. Rittle et al., *J. Org. Chem.*, 47, 3016 (1982); M. H. Gelb et al., *Biochemistry*, 24, 1813 (1985); J. A. Fehrentz et al., *Biochem. Biophys. Res. Comm.*, 185, 865 (1992); J. M. Travins et al., *Org. Lett.*, 3, 2725 (2001); R. K. Hom et al., *J. Med. Chem.*, 47, 158 (2004); and hydroxyethylene isosteres (G. B. Dreyer et al., *Biochemistry*, 31, 6646 (1992); J. Konvalinka et al., *Eur. J. Biochem.*, 270, 559 (1997); M. S. Shearman et al., *Biochemistry*, 39, 8698 (2000)). Protease dependent diseases which can be targeted using such compounds include hepatitis, AIDS, Alzheimer's disease, malaria and cancer, among others. The penicillin-binding proteins (PBPs) are also excellent targets for this synthetic method. New PBP inhibitors also are candidates as new antibacterial agents. The present invention also provides the possibility of assembling a series of such peptide mimetic functional groups together to form novel peptide like polymers with novel and valuable properties, all based on the use of suitably side chain-protected amino acid t-butyl esters as fundamental building blocks combined with available carboxy group and carboxy group derivative elaboration chemistry.

DETAILED DESCRIPTION OF THE INVENTION

Figure 1:
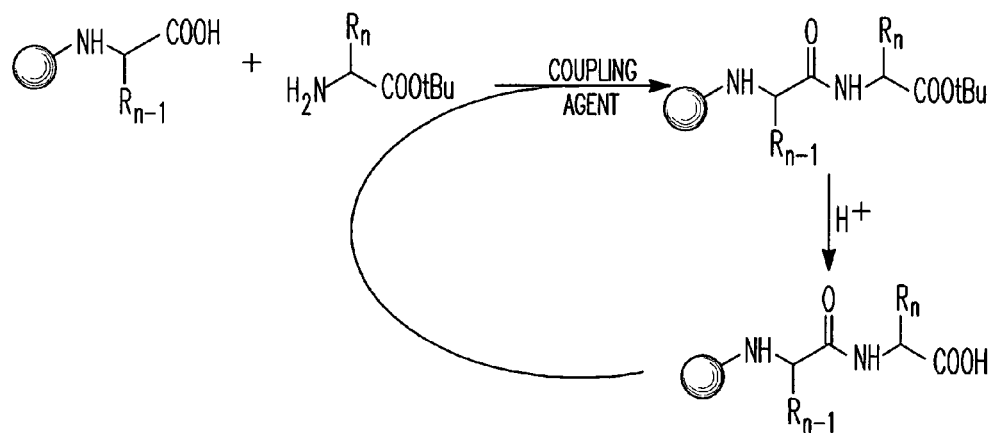
FIG. 1 summarizes the present method (CHR$_{n-1}$ represents the residue of the N-terminal amino acid; CHR$_n$ is the residue of the second amino acid added, etc.).

The present method provides a simple and effective method for synthesizing peptides in the N-to-C direction, based on amino acid t-butyl esters, as shown in FIG. 1. This method takes advantage of the availability of a number of amino acid t-butyl esters, and a list of currently commercially available amino acid t-butyl esters appropriate for reverse peptide synthesis is given in Table 1. This list provides suitable derivatives to prepare L peptides containing all the standard L amino acids except Asp, Cys, and Ser, as well as a number of non-standard and D amino acids. Additional suitable side chain protected amino acid tBu esters can be prepared by standard methods (Bodanszky, M., Peptide chemistry: A practical textbook. Second, revised ed. 1993, Berlin, Heidelberg: Springer-Verlag at 217).

TABLE 1

Commercially available amino acid t-butyl esters from Bachem appropriate for N-to-C peptide synthesis.

| Ala-OtBu | Gln-OtBu | D-Leu-OtBu | D-Pro-OtBu |
|---|---|---|---|
| D-Ala-OtBu | Glu(OMe)-OtBu | Lys(Z)-OtBu | Sar-OtBu |
| β-Ala-OtBu | Glu(OtBu)NH$_2$ | Met-OtBu | Thr-OtBu |
| Arg(Mtr)-OtBu | Gly(OtBu)-OMe | Orn(Z)-OtBu | Trp-OtBu |
| Asn-OtBu | Gly-OtBu | Phe-OtBu | Tyr-OtBu |
| Asp(OtBu)-NH$_2$ | His(1-Trt)-OtBu | Phg-OtBu | D-Tyr-OtBu |
| Asp(OtBu)-OMe | Ile-OtBu | Pro-OtBu | Val-OtBu |
| | Leu-OtBu | | D-Val-OtBu |

All amino acids are L unless otherwise indicated. Abbreviations: Standard amino acids have their normal abbreviations. Other Abbreviations: Mtr = 4-methoxy-2,36-trimethylbenzenesulfonyl, Orn = ornithine (2,5-diaminopentanoic acid), OtBu = O-t-butyl, Phg = L-phenylglycine, Sar = sarcosine (N-methyl glycine), Trt = trityl.

A number of conditions are expected to affect both coupling efficiency and quality (racemization) of the final product. Syntheses can be monitored for overall yield and purity by HPLC and for racemization using Marfey's reagent (Marfey, Calsberg Res. Commun., 49, 591 (1984); Adamson et al., Anal. Biochem., 202, 202 (1992)).

In normal (C-to-N) peptide synthesis, an excess of the activated carboxyl component is used to drive the reaction to completion. In N-to-C synthesis, the carboxyl group is anchored and cannot be generated in excess. This problem can be solved by using carbodiimides, or other coupling reagents, which can be used in the presence of the carboxyl component, and an excess of the amine component. A second difficulty concerns which protection chemistry to use for the carboxyl group of the amino component. One recent report (Johansson et al., cited above (2000)) describes the use of amine components with a silyl-protected carboxyl group, the use of a photolabile attachment to the solid support, and the use of HATU, O-(7-azabenzotriazol-1-yl)-N,N,N',N'-tetramethyluronium hexafluorophosphate; or TATU (O-benzotriazol-1-yl-N,N,N',N'-tetramethyluronium tetrafluoroborate) as coupling agents. HBTU, and PyBOP can also be used as coupling agents.

In the present method, these reagents can be used in about 2 to 10-fold molar excess over resin attached functional groups. Bases such as 2,4,6-trimethylpyridine (TMP), diisopropyl amine (DIEA), and N-methylmorpholine (NMM) can be used at about 2 to 10-fold molar excess. The amino acid concentration can be used in about 2 to 10-fold molar excess as discussed above. Mixtures of CH$_2$Cl$_2$/DMF can be employed as solvents.

Figure 8:
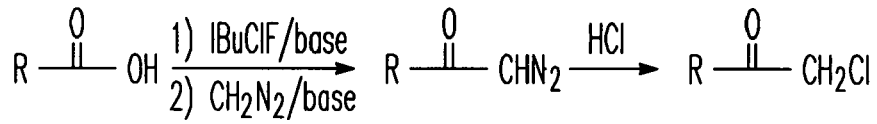
FIG. 8 depicts a synthetic route of chloromethyl ketones.
Figure 9:
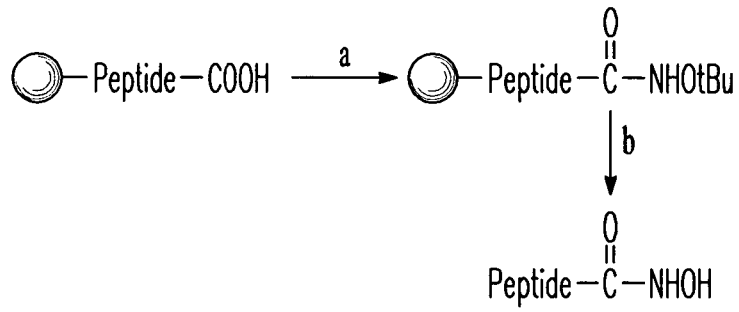
FIG. 9 depicts a route to peptide hydroxamic acids.

A free N-terminal amino group is generated by cleavage of the immobilized peptides using Glu or Gln linkers using the Suc/Glu/Gln linker strategy, or from peptides synthesized using the Dde or Urethane strategies (FIGS. 8-10), or from peptide synthesized using the BAL (FIG. 11) strategy if a strong acid-sensitive capping group for the secondary amine attachment is used, such as an Fmoc or Cbz capping/protecting group.

Attaching the nascent peptide to the resin using a Glu/Gln linker strategy, yields product peptides and peptide mimetics that all have a Glu or Gln residue at their N-terminus. However, it can be preferable to have product peptide without a linker on the N-terminus, for example comprising a free N-terminus. In accord with the present method, peptides/mimetics can now be synthesized with a wide variety of N-terminal substituents, or without a substituent, or as cyclic peptides.

The methods described herein are focused on both resin attachment strategies, and C-terminal functional group elaboration strategies. The urethane strategy described by Felix and Merrifield, by Letsinger, cited above, and by R. Leger et al., Tetrahedron Lett., 39, 4174 (1998), is also useful with the present t-butyl ester based synthesis and was successfully implemented for the t-butyl ester based inverse peptide synthesis. Using this strategy peptides and peptide mimetics are obtained with a free N-terminus and with all side chains deprotected during the TFMSA/TFA cleavage reaction conditions.

A Dde based strategy has not been described previously for inverse peptide synthesis. The Dde functional group is used to protect amines in organic chemistry (T. W. Green and P. G. M. Wuts, Protecting Groups in Organic Synthesis, 3d ed. J. Wiley & Sons (1999) and references therein). Dde based resins have been described in the literature for anchoring and protecting amines for solid phase chemistry, and are commercially available (NovaBiochem). See, e.g., M. E. Attardi et al. Tetrahedron Lett., 41, 7391 (2000); S. R. Chhabra et al., Tetrahedron Lett., 41, 1095 (2000); Ibid. at 1099.

In the attachment strategies referred to above, based on the use of a Succinyl/Glu/Gln linker strategy, a urethane attachment strategy, or a Dde attachment strategy, the attached amine of the N-terminal amino acid is rendered unreactive by the attachment method. An alternative to this type of approach is to attach a primary amine to suitably reactive solid phase benzylic carbon, to generate an anchored secondary amine. The benzylic secondary amine is suitable for further reaction, such as acylation, and eventual cleavage of the benzylic attachment to provide the desired product. This approach was reported for use in preparing fully protected peptide ethyl esters using a photocleavable nitrobenzylhalide resin (M. Renil et al., Tetrahedron Lett., 35, 3809 (1994)). In this approach an amino acid ethyl ester was attached to a nitrobenzylhalide resin, and standard Boc based C-to-N synthesis cycles used to elaborate the peptide chain. Photolytic cleavage of the benzylic resin-amide attachment provided the fully protected peptide esters. Benzylic attachment has been used to anchor amino acid ester monomers as intermediates in benzodiazepine library synthesis by Ellman and coworkers (C. C. Boojamra et al., *J. Org. Chem.* 60, 5742 (1995)). In this approach an amino acid ester was loaded onto a 4-oxy-2,6-dimethoxybenzaldehyde (dimethoxy) based resin by reductive amination, followed by elaboration into a benzodiazepine, which was finally cleaved from the resin by acidolysis. Benzylic attachment has also been investigated as a way to anchor various amino acid esters for C-to-N based synthesis of C-terminally modified peptides (Backbone Amide Linker (BAL) approach) (K. Jensen et al., *J. Amer. Chem. Soc.*, 120, 5441 (1998); G. T. Bourne et al., *J. Org. Chem.* 64, 3095 (1999); V. Boas et al., *J. Comb. Chem.*, 4, 223 (2002); J. Alsina et al., *J. Org. Chem.* 64, 8761 (1999)). Patents have been issued on certain aspects of this technology (See, e.g., U.S. Pat. Nos. 6,566,494 and 5,917,015).

Approaches for loading the first residue onto the resin for the BAL attachment strategy include the synthesis of a suitable amino acid ester-linker construct, which is then attached to a suitable resin (K. Jensen et al., *J. Amer. Chem. Soc.*, 120, 5441 (1998); G. T. Bourne et al., *J. Org. Chem.*, 64, 3095 (1999); V. Boas et al., *J. Comb. Chem.*, 4, 223 (2002)). For combinatorial library synthesis direct attachment of an amino acid ester to a suitable resin would be preferable. One approach to direct attachment is through direct displacement of on-resin benzyl halides or other leaving groups (M. Renil et al., *Tetrahedon Lett.*, 35, 3809, (1994); K. Ngu et al., *Tetrahedron Lett.*, 38, 973 (1997); B. Raju et al., *op. cit.*, 38, 4965 (1997)). However, loading by reductive amination of an amine or an amino acid ester onto a benzaldehyde based resins is a generally preferred approach, using suitable mild borohydride based reducing agents such as $NaBH(OAc)_3$ (Boojamra et al., cited above; T. A. Okayama et al., *Org. Lett.*, 2, 1787 (2000)) or $NaBH_3CN$ (G. T. Bourne et al., *Tetrahedron Lett.*, 40, 7271 (1999)).

Figure 11:
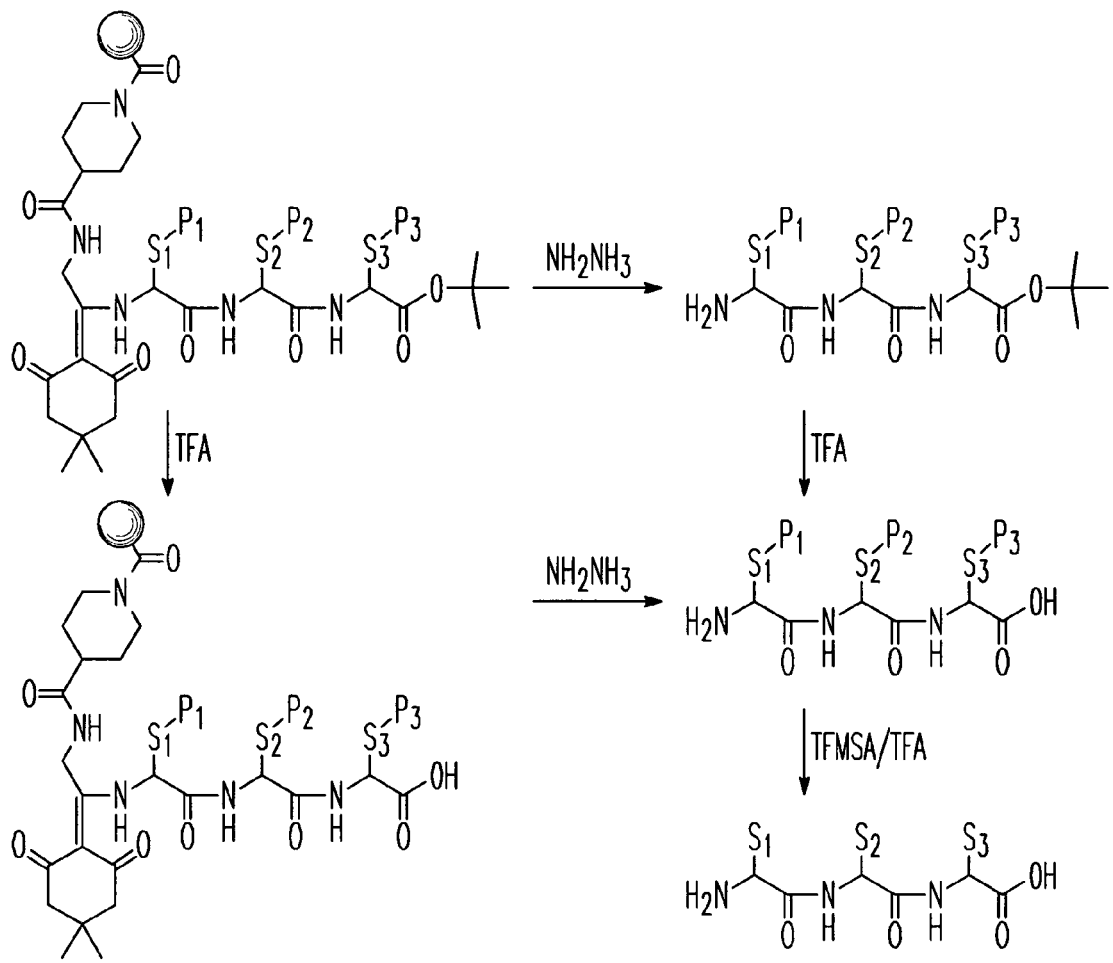
FIG. 11 depicts conversions of Dde resin-attached peptides, wherein S—P represent sidechain-protecting group pairs.
Figure 12:
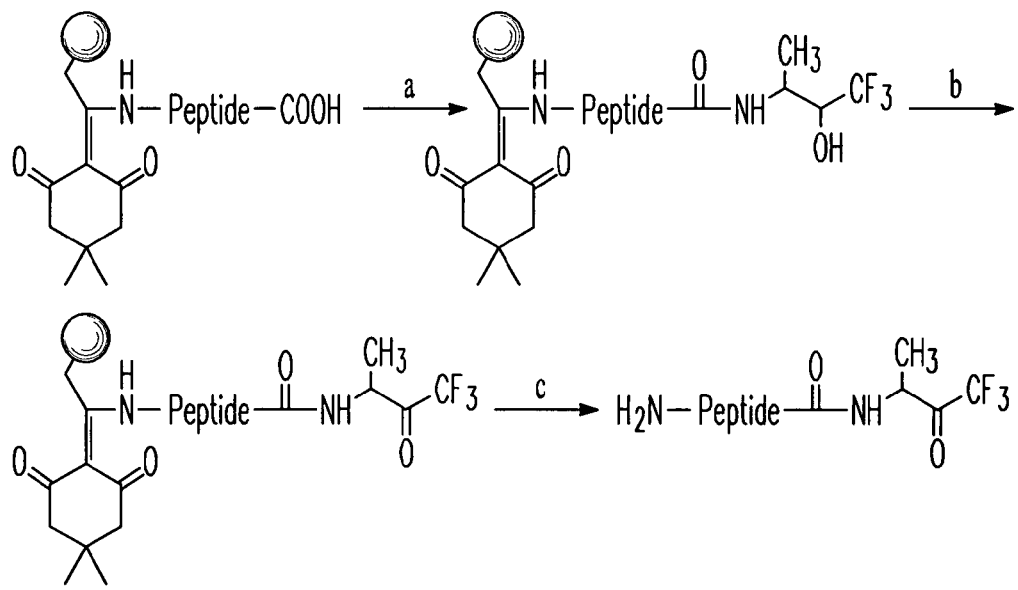
FIG. 12 depicts a Dde resin-based inverse synthesis of peptide trifluoromethyl ketones.

As discussed above, there are certain advantages to an N-to-C based synthesis strategy for C-terminally modified peptide mimetics. However, the ability to selectively modify the N-terminus of a solid phase peptide chain is also desirable. Combining amino acid t-butyl ester based ISPPS with a BAL attachment strategy provides both N and C-termini of the resin bound peptide/mimetic for modification (FIGS. 11-12). In this approach, the first amino acid t-butyl ester is attached directly onto a benzaldehyde or benzyl halide based resin, followed by capping of the secondary amine attachment with a suitable acyl, urethane, ureido, or sulfonyl group, and then followed ISPPS cycles using the t-butyl ester based approach described herein. Using a suitable protecting group to cap the secondary amine (eg. Fmoc) allows the secondary amine to be selectively revealed for further modification at any point in peptide/mimetic synthesis. Protection with Cbz or other moderate acid-stable protecting groups (Cl-Cbz is more acid stable than Cbz (M. Bodanszky et al., The practice of peptide synthesis, Berlin/Heidelberg, Springer-Verlag (1994)) and preferable in this application), which is stable to t-butyl ester based ISPPS, will be removed during cleavage of the peptide/mimetic from the resin to provide a peptide/mimetic with a free N-terminus. Finally, moderate and strong acid-stable capping groups (acyl, sulfonamido, ureido, etc.) will remain in the product peptides, and can be included to provide additional diversity in product peptides/mimetics.

These linking methods (Suc/Glu/Gln, Dde, Urethane, BAL) provide several approaches for anchoring a peptide/mimetic during t-butyl ester based inverse solid phase peptide synthesis, and can provide different products with a significant level of versatility. For example, the Suc/Glu/Gln method can provide peptides/mimetics with an N-terminal Succinyl, Glu, or Gln residue.

The urethane strategy can provide peptides with a free amino terminus and with sidechain protecting groups removed.

The Dde strategy for inverse peptide synthesis can provide peptides with a free N-terminus, and either with or without side chain and a carboxy terminal protecting group.

Figure 14:
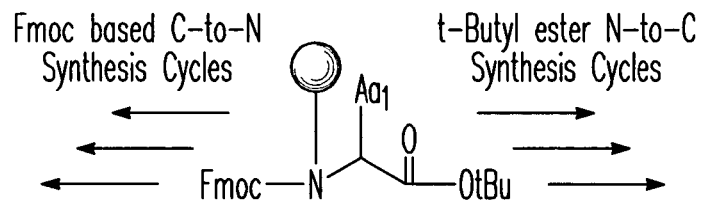
FIG. 14 depicts a scheme for bidirectional peptide synthesis.

The backbone attachment (BAL) strategy has been used previously for normal direction peptide synthesis, but not for ISPPS. As shown in FIG. 14, the backbone attachment strategy can provide both N and C termini for further elaboration, and also for cyclization, and can provide a highly versatile approach to peptide mimetic synthesis.

During the course of peptide synthesis using the described methods, the extent of coupling is currently qualitatively assessed by testing for free carboxyl groups using a Malachite Green test (Attardi et al., *Tet. Lett.*, 41, 7391 (2000)). For the BAL attachment method, loading and capping reactions can be qualitatively assessed using a chloranil based test for secondary amines (J. Blake et al., *Int. J. Peptide Protein Res.*, 7, 495). In some cases, sequence data from peptides might be useful and approaches for C-terminally sequencing peptides are now available (Samyn et al., *Anal. Biochem.*, 72, 1389 (2000)).

For the Suc/Glu/Gln linker strategy, these different resins have been tested—hydroxymethyl polystyrene and Pam resin (4-hydroxymethylphenylacetamido-methyl polystyrene) and MBHA (4-methyl-benzhydryl amino polystyrene). To provide the initial carboxyl group, a succinyl linker was used in preliminary studies. Some loss of polypeptide was observed during TFA (trifluoroacetic acid) deprotection of t-butyl esters on hydroxymethyl polystyrene resin, but not significantly with Pam resin, and Pam resin was used in subsequent studies. MBHA forms an amide linkage with the Glu linker that cleaves to an N-terminal glutamine (Glu) residue on the free peptide.

Figure 2:
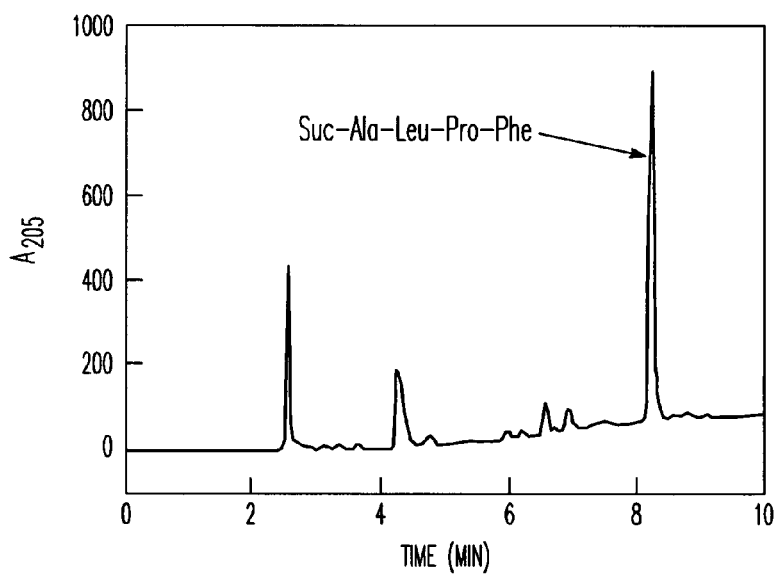
FIG. 2 is a reverse phase of HPLC of an inverse peptide (SEQ ID NO: 1) prepared by the present method.

The coupling strategy uses a ten-fold excess of base (DIPLA or TMP), a five-fold excess of coupling reagent (DCC/HOBT, HBTU, or HATU) and a ten-fold molar excess of $NH_2$—A—C(O)—OtBu. Excess coupling reagent and amine can be washed away after coupling is complete. A number of such coupling reagents are known. Three have been tested to date: (O-(7-azabenzotriazol-1-yl)-N,N,N',N'-tetramethyluronium hexafluorophosphate)(HATU), dicyclohexylcarbodiimide (DCC)/hydroxybenzotriazol (HOBT) and O-benzotriazol-1-yl-N,N,N',N'-tetramethyl uranium hexafluorophosphate (HBTU). The coupling methods have been tested by comparison of syntheses of the succinylated peptide Suc-Ala-Leu-Pro-Phe (FIG. 2).

EXAMPLE 1

Preparation of Oligopeptide Using Succinylated Resin

Starting with commercial Pam resin, the resin was first succinylated using succinic anhydride to provide a carboxyl group for subsequent coupling steps. Succinylation was selected for initial work since many protease related synthetic peptides are prepared with an N-terminal succinyl group. Succinylated resin was then subjected to HBTU-mediated coupling of L-Ala-OtBu (L-Ala-t-butyl ester) with DIEA (diisopropylethylamine) as base. Subsequently, the t-butyl ester was deprotected with 25% TFA/DCM (1×5 seconds, filter, then 1×30 min). This process was repeated with each subsequent amino acid t-butyl ester (Ala, Pro, Phe to give Suc-Ala-Leu-Pro-Phe; SEQ ID NO:1). Finally, the peptide was liberated from the polymer using TFMSA (trifluoromethanesulfonic acid)/TFA cleavage. The final product (FIG. 2) was the desired product, and its identity was confirmed by HPLC-MS comparison with commercially available authentic Suc-Ala-Leu-Pro-Phe (SEQ ID NO:1).

EXAMPLE 2

Comparison of Coupling Agents and Linkers

Using the Marfey's reagent based method cited above, HBTU/DIEA and HATU/TMP coupling procedures have been compared for synthesis of the test peptide Suc-Ala-Leu-Pro-Phe (SEQ ID NO:1) as summarized in Table 2.

TABLE 2

| % D-isomer found in peptide Suc-Ala-Leu-Pro-Phe | | | | |
| --- | --- | --- | --- | --- |
| | Ala | Leu | Pro | Phe |
| HBTU-coupling | 27% | 23% | <2% | <2% |
| HATU-coupling | 38% | 5% | <2% | <2% |

With both coupling procedures >20% racemization of the first residue attached to a succinyl linker is observed. HATU/TMP provides less racemization in general than HBTU or DCC/HOBT, and HATU shows ≦5% racemization of subsequent residues even for the more difficult praline coupling. The observation of high racemization of only the first residue following the succinyl linker suggested that a protected α-amino group in a linker might reduce racemization of the first added residue.

Z-Glu-OtBu (Z=Cbz) was therefore tested as a linker. Z-Glu-OtBu was coupled to PAM resin using HATU-based coupling protocol, followed by the standard deprotection and coupling procedure. This modification resulted in <5% racemization of the residues in synthesized peptides. Peptides synthesized with this linker strategy have a Glu residue as the N-terminus (Glu linker strategy). To avoid the possibility of esterolytic cleavage of the resin-Glu attachment, we have also tested the use of an amide attachment strategy by coupling Z-Glu-OtBu to MBHA resin, a resin generally used in normal direction peptide synthesis to general C-terminally amidated peptides. Cleavage from this resin provides an N terminal Gln residue (i.e., amidated Glu side chain) (Gln linker strategy). This linker strategy also provided peptides with low (<5%) racemization in test syntheses. The increased stability of an amide link to the resin may prove useful for some carboxyl group modification methods. One advantage of both the Glu and Gln linker strategies over the succinyl linker strategy is that they provide the free N-terminal α-amino group of the terminal Glu or Gln residue, which could then be used to attach a multiplicity of peptides to derivatized substrates such as to silicon wafers or glass slides comprising free CHO groups, to yield "chip" libraries useful for very high throughput screening (cf., MacBeath and Schreiber, *Science*, 289, 1760-176 (2000)).

EXAMPLE 3

Inverse Peptide Synthesis Using MBHA Resin

MBHA-Z-Glu-OtBu resin (linked between the γ-carboxyl of Z-Glu-OtBu and the amino of MBHA resin) was employed. MBHA is a 4-methyl-benzhydryl amine polystyrene resin. The coupling method used is the HATU/TMP-mediated activation. Details of this method are described below.

1. Attachment of the Linker (Z-Glu-OtBu)

MBHA resin (1.0 equiv.) is first washed with DMF, 20% DIEA/DMF, DMF and DCM. To this pre-washed resin, a solution of Z-Glu-OtBu (5.0 equiv.) wherein Z is benzyloxycarbonyl, HATU (5.0 equiv.) and TMP (5.0 equiv.) in DMF is added. The suspension is stirred at room temperature for 3 h. The resin is then filtered and washed with DMF and DCM. The resulting resin is treated with a solution of acetic anhydride (3.0 equiv.) and DIEA (3.0 equiv.) in DMF for 30 min (to cap any remaining on-resin amine groups). The resin is filtered and washed with DMF and DCM.

2. Deprotection of tBu Group

Above resin is treated with 25% TFA in DCM (1×5 s) and 50% TFA in DCM (30 min×1). The resin is then washed with DCM×3, NMP×2, DCM×3, dried.

3. On-Resin Assembly of Peptide-Chain

The Z-Glu-linked resin is treated with a solution of an amino acid OtBu ester (5.0 equiv. usually HCl salt), HATU (5.0 equiv.) and TMP (10.0 equiv., 5 equiv. if amino acid is free base and not HCl salt) in DMF. The suspension is stirred at room temperature for 2 h. The resin is then filtered and washed with DMF and DCM. A small amount of resin sample (15 mg) is removed and subjected to a color test reaction using 1 ml of 0.25% Malachite Green (in ethanol) along with 1 drop of triethylamine. A double coupling is performed if the testing shows positive (green or blue on resin). If the testing gives negative result (no color on resin), then repeat step 2 and step 3 until reaching the desired length of peptide.

4. Cleavage of Peptide from the Resin

Before cleavage, the C-terminal protecting group (t-Bu) was removed using the identical procedure described in step 2. After being washed and dried, the deprotected peptide-resin is treated with a mixture of TFA (100 μl) and TFMSA (10 μl) for about 1 h. The solution (crude product) is collected by filtration, dried under a nitrogen stream and was analyzed by HPLC and LC/MS.

EXAMPLE 4

Urethane Attachment Strategy

Figure 3:
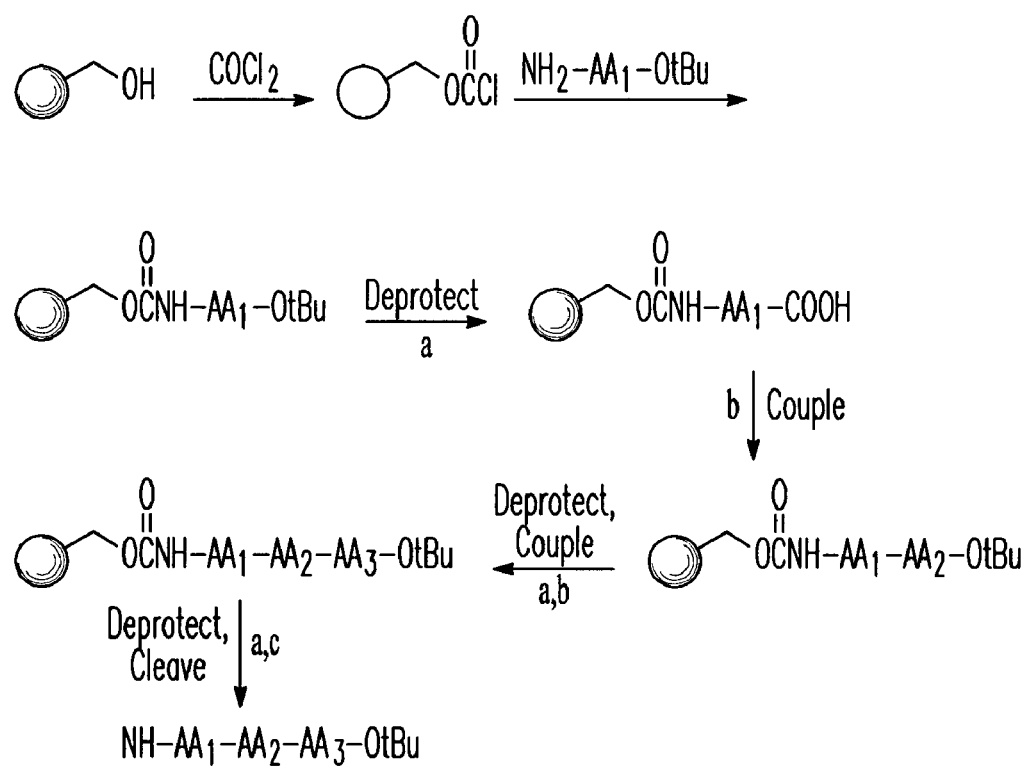
FIG. 3 depicts a urethane attachment strategy for ISPPS (•=resin matrix).

The attachment and ISPPS strategy are outlined in FIG. 3. Hydroxymethyl polystyrene resin (Advanced Chemtech) (100 mg) (0.1 mmol) was converted to the chloroformate by treating with 10 equivalents of phosgene in DCM for 30 min and then drying under vacuum. The first amino acid was then loaded onto the resin by adding a solution of 10 equivalents of amino acid t-butyl ester and 5 equivalents of DIPEA in DMF to the dried resin, and stirring for 4 hrs. To assess loading efficiency, Phe was used as the first residue, and after loading and washing the resin was treated with 10% TFMSA/TFA for 1 hr. Total Phe attached to the resin was quantitated by HPLC. For ISPPS, the first residue was deprotected with 50% TFA/DCM, and synthesis cycles performed as outlined in Table 3.

TABLE 3

| ISPPS protocol. | | |
| --- | --- | --- |
| Description | Reagent | Repetition and Duration |
| OtBu Deprotection | 25% TFA/DCM | 1 × 5 s |
| | 50% TFA/DCM | 1 × 30 min |
| Washes | DCM | 3 × 5 s |
| | NMP* | 2 × 5 s |
| | DCM | 3 × 5 s |
| Activation/ Coupling | 5 × HATU 5 × AA-OtBu•HCl 10 × TMP in DMF | 12 h |
| Washes | DCM | 3 × 5 s |
| | DMF | 3 × 5 s |

*N-methyl pyrrolidinone

Cleavage from the resin was accomplished with 10% TFMSA/TFA. Seven tripeptides were synthesized as representative model peptides in high purity (>80% by HPLC) (Table 4).

TABLE 4

Molecular weight confirmation and purities of the synthesized peptides and peptide mimetics.

| | | Mol Wt | | |
|---|---|---|---|---|
| | Sample | Calcd | Found[a] | Purity[b] |
| 1 | Tyr-Ala-Phe | 399.2 | 399.8 | 88% |
| 2 | Tyr-Gly-Orn | 352.3 | 352.7 | 92% |
| 3 | Tyr-Ala-Val | 351.5 | 351.8 | 89% |
| 4 | Asn-D-Val-Leu | 344.3 | 344.8 | 87% |
| 5 | Asn-Leu-Glu | 374.2 | 374.8 | 81% |
| 6 | Gly-Ile-Thr | 289.2 | 289.7 | 82% |
| 7 | Phe-Ala-Gly | 293.1 | 293.6 | 81% |
| 8 | Asn-Leu-Glu-boroAla (SEQ ID NO: 2) | 427.2 | 427.8 | 74% |
| 9 | Phe-Ala-Gly-boroAla (SEQ ID NO: 3) | 346.1 | 346.7 | 75% |
| 10 | Tyr-Ala-Phe-NHCH($CH_3$)COCF$_3$•$H_2O$ | 522.2 | 525.0 | 74% |
| 11 | Tyr-Ala-Orn-NHCH($CH_3$)COCF$_3$•$H_2O$ | 475.7 | 477.9 | 74% |
| 12 | Phe-Ala-Gly-NHOH | 308.1 | 308.7 | 81% |
| 13 | Phe-Leu-Val-NHOH | 392.4 | 392.9 | 79% |

[a]Determined on an aQa ThermoQuest (Finnigan) system equipped with atmospheric-pressure ionization (API) electro spray source.
[b]Determined by HPLC analysis of the crude product at 260 nm on a Hewlett-Packard series 1050 system equipped with a C18 column (Solvent miser, 2.1 x 250 mm, 5.0 µM particles). Compounds were separated by gradient elution; 0% of solvent B (0.1% TFA in 70% aqueous acetonitrile) in solvent A (0.1% TFA in water) for 1 min, then 0% to 100% of solvent B in solvent A in 10 min, then 0% to 100% of solvent C (0.095% TEA in acetonitrile) in solvent B in 5 min.

These peptides were analyzed for amino acid racemization using Marfey's reagent. The observed racemization of individual amino acids was less than 2% (Table 5).

TABLE 5

| Peptide | $AA_1$ | $AA_2$ | $AA_3$ |
|---|---|---|---|
| Tyr-Ala-Phe | D-Tyr (1.2%) | D-Ala (1.4%) | D-Phe (1.0%) |
| Tyr-Gly-Orn | D-Tyr (1.3%) | — | D-Orn (1.2%) |
| Tyr-Ala-Val | D-Tyr (1.2%) | D-Ala (1.2%) | D-Val (1.4%) |
| Asn-D-Val-Leu | D-Asn (1.4%) | L-Val (1.5%) | D-Leu (1.1%) |

To demonstrate the utility of this approach for C-terminally modified peptide mimetic synthesis, several peptide mimetic classes were synthesized using this approach. A peptide trifluoromethylketone was synthesized following the procedures described herein and in W. G. Gutheil et al., *Chem. Pharm. Bull.* (Tokyo), 50, 688 (2002) (Example 4(C)). A peptide boronic acid was also synthesized by coupling DL-boroAla (See, A. Pechenov et al., *Biochem.*, 42, 579 (2003) and Example 4(A), below) to the resin in the last synthesis cycle. Peptide boronic acids have been of high interest as potential drugs and Velcade, recently approved for treatment of multiple myeloma, is a peptide boronic acid.

This strategy should be readily applicable to peptide aldehydes and chloromethyl ketones. Peptide aldehydes and chloromethyl ketones are versatile synthetic intermediates and can be elaborated into a wide variety of functional groups. See Example 4(B) and (D), above.

EXAMPLE 5

Introduction of Common Inhibitor Functional Groups, such as Peptide Aldehyde, Chloromethyl Ketone, Fluoromethyl Ketone, and Boronic Acid, onto the C Terminus of Solid Phase Attached to N-to-C Peptide Chains In preliminary studies, solution phase methods have been used to synthesize a representative example of each of these inhibitor classes. For solid phase syntheses, two distinct strategies are used to prepare this set of four inhibitor classes.

In the case of boronic acids and trifluoromethylketones, suitably derivatized inhibitor monomers must be prepared and introduced into the peptide chain. In the case of chloromethylketones and aldehydes, direct chemical modification of the C terminus can provide the desired functional group.

A. Boronic Acid (boro-Ala) Based Peptides

The chemistry required to prepare boroAla and several other hydrophobic amino acid analogs such as boroVal is well known (Kettner & Shenvi, *J. Biol. Chem.*, 259, 15106 (1984); Matteson & Sadhu, U.S. Pat. No. 4,525,309 (1985)). See FIG. 3. Boro-Ala can be introduced onto the C-terminus of a peptide using the standard procedures for adding an amino acid to a peptide chain.

Figure 4:
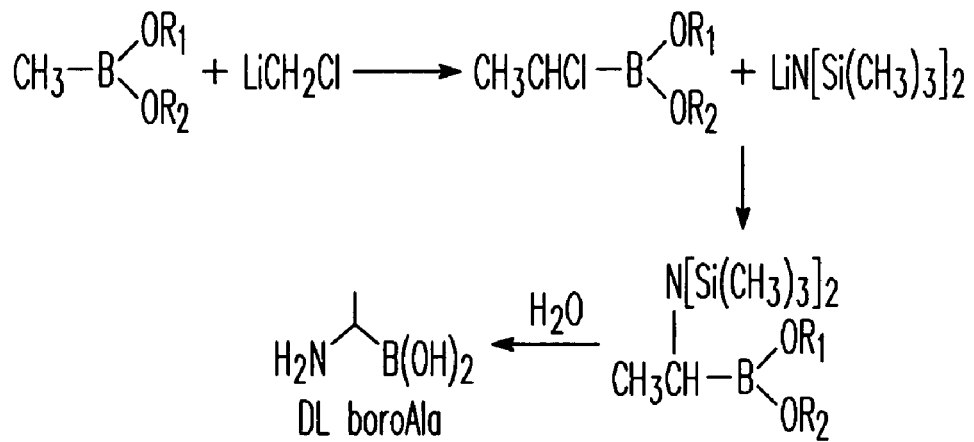
FIG. 4 is a summary of the preparation of DL-boroAla.
Figure 5:
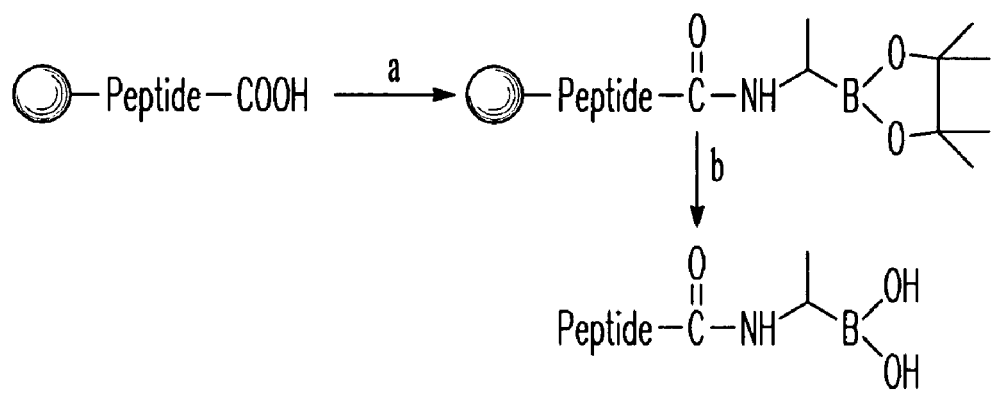
FIG. 5 depicts a route to peptide boronic acids.

Peptide boronic acids were synthesized based on the approach outlined in FIG. 5. The boroAla-pinacol derivative was synthesized as described previously (FIG. 4). Resin loaded with Phe-Ala-Gly or Ans-Leu-Glu was coupled with boroAla-pinacol (HCl salt) using the standard HATU/TMP coupling protocol, followed by cleavage with 10% TFMSA/TFA to give the corresponding peptide boronic acids.

B. Peptide Aldehyde Based Peptides

Figure 6:
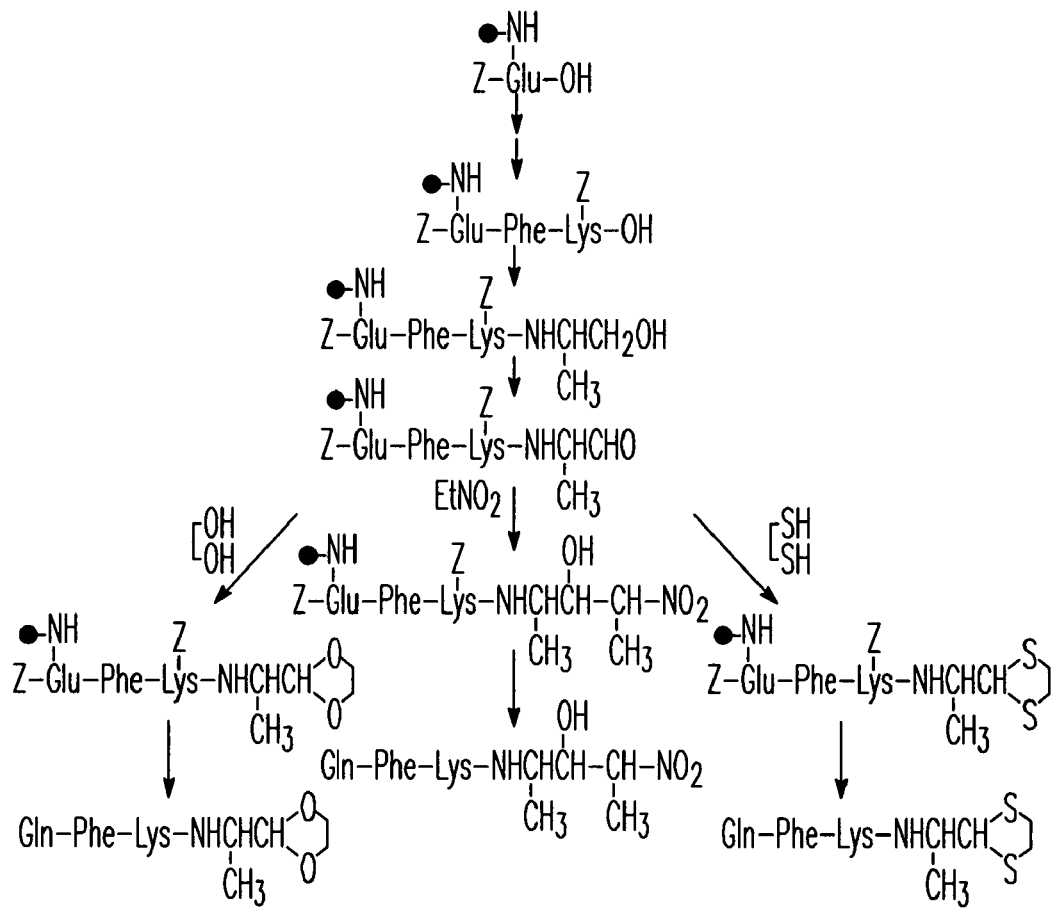
FIG. 6 depicts the synthesis, protection and derivatization of peptide aldehydes.

As shown in FIG. 6, several strategies for the synthesis of peptide aldehydes have been described, including from amino alcohols by oxidation (Thompson, *Biochem.*, 12, 47 (1973); Okura & Swern, *Tetrahedron*, 34, 1651 (1978)), by reduction of the amino acid methyl esters with diisobutylaluminum hydride (DIBAL) (Ito et al., *Biochem. Biophys. Res. Comm.*, 49, 343 (1975)); Gorenstein & Shaw, *Biochem.*, 21, 4679 (1982)), or by reduction of Weinreb N-methoxy-N-methylcarboxamides with LiAlH$_4$ (Fehrentz & Castro, *Synthesis*, 676 (1983)). The best solution phase method tested so far is reduction of Weinreb amides. This method works well in the presence of Boc and Cbz groups, but may be incompatible with most esters, for example in amino acid side chain protecting groups for Glu and Asp.

The successful Pfitzner-Moffat oxidation (DCC/$Cl_2HCO_2H$/DMSO) of peptide trifluoroamino alcohols suggests this strategy could also work for synthesis of peptide aldehydes as outlined in FIG. 6. This approach was tested, and was successful in generating an on-resin aldehyde. Two problems appeared to affect the yield of the peptide aldehyde product. The first was competition between N and O coupling with the amino alcohol monomer. N coupling resulted in the desired final product, whereas O coupling gave a labile ester intermediate which was cleaved during the resin cleavage reaction to provide the starting peptide. The second problem was that the product peptide aldehyde was somewhat labile to the TFMSA/TFA cleavage conditions. To avoid N and O competition, the OH group in the amino alcohol monomer can be protected by a suitable protecting group. Use of t-butyl has been reported (K. J. Jensen et al., *J. Amer. Chem. Soc.*, 120, 5541 (1998)). However, the t-butyl group was difficult to incorporate into an amino alcohol precursor, presumably because of electrostatic interaction with the protonated free amino group. Good results were however obtained with acid catalyzed (5% TFA/$CH_2Cl_2$) addition of dihydropyran to the amino alcohol to give the tetrahydropyran (THP) adduct of the OH functional group, which is a very easy one pot reaction, followed by drying under vacuum. For the t-butyl ether protecting group, TFA deprotection provides the peptide alcohol (as cited above). For THP, 5% TFA/10% MeOH/85%$CH_2Cl_2$ gave good results for peptide alcohol synthesis.

To avoid the problem of aldehyde degradation under TFMSA/TFA cleavage conditions, the aldehyde can be protected by treatment with a 20-fold excess of ethylene glycol in 5% TFA/DCM followed by cleavage from the resin provided the protected aldehyde (Gln-Phe-Lys-Ala-CH($OCH_2$)$_2$ (SEQ ID NO:4) as the major peptide product ([M+H]=522.8). Impurities were: a) Gln-Phe-Lys ([M+H]=421.5) due to incomplete coupling of the amino alcohol, b) Gln-Phe-Lys-Ala-$CH_2$OH([M+H]=486.6) (SEQ ID NO:4), due to incomplete oxidation of the amino alcohol, and c) an unknown impurity ([M+H]=574.8). Reaction of on resin peptide aldehyde with nitroethane and dithioethane have also been tested and give complete conversion of the aldehyde to the expected derivatives (FIG. 6). In FIG. 6, Z=benzyloxycarbonyl, •=resin, and Z-Glu-OtBu is $PhCH_2OC(=O)NHCH(CH_2CH_2CO_2H)$—$CO_2tBu$.

A large number of commercially available nucleophiles (cf. anion of nitroethane) can be reacted with on-resin aldehydes to provide peptide aldehyde adduct libraries of tremendous diversity (FIG. 6). Dithiane and other derivatives provide the further possibility of acyl-anion equivalent chemistry, which would allow peptide aldehydes to be further elaborated using various alkylating agents into peptide mimetic ketones (see, Seebach et al., *J. Org. Chem.* 40, 231 (1975); Hase et al., *Aldrichimica Acta*, 14, 73 (1981)).

C. Trifluoromethylketone-Based Peptides

Figure 7:
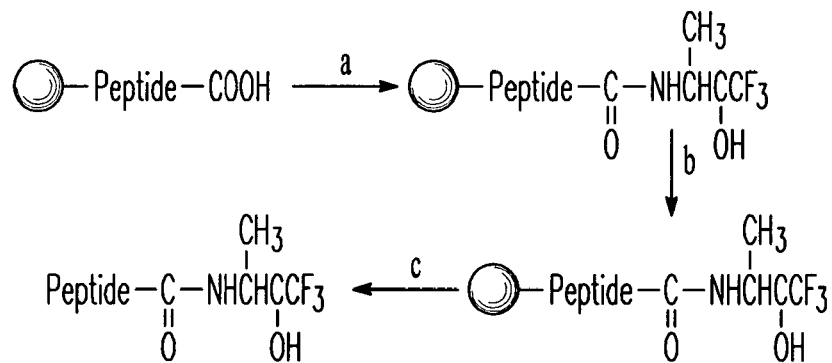
FIG. 7 depicts a synthetic route to peptide trifluoromethyl ketones.

The classic procedure for preparing peptide trifluoromethylketones is shown in FIG. 7 (Imperiali & Abeles, *Tet. Lett.*, 22, 135 (1986)). Oxidation of the acyl trifluoromethyl aminoalcohol can be performed with $KMnO_4$, but can also be performed with a modified Pfitzner-Moffat (carbodiimide/$Cl_2HCO_2H$/DMSO) procedure (Fearon et al., *J. Med. Chem.*, 30, 1617 (1987)) (FIG. 7), or with a Dess-Martin periodinane (1,1,1-triacetoxy-2,1-benzoxiodol-3-(3H)-one) procedure (Edwards et al., U.S. Pat. No. 5,194,588 (1993); Dess & Martin, *J. Org. Chem.*, 48, 4155 (1983)).

Two peptide trifluoromethylketones were synthesized using the approach outlined in FIG. 7. The precursor aminotrifluoromethylalcohol was synthesized as described previously by A. Pechenov et al., *Biochemistry*, 42, 579 (2003). Resin loaded with Tyr-Ala-Phe or Tyr-Gly-Om was coupled with this aminotrifluoromethylalcohol using the HATU/TMP coupling procedure to give the corresponding peptide trifluoromethylalcohols. Oxidation of the on resin trifluoromethylalcohols was performed by Pfitzner-Moffat oxidation to give the corresponding peptide trifluoromethylketones, which were then cleaved from the resin using 10% TFMSA/TFA. Peptide trifluoromethylketones were detected in LC/MS as their hydrates. The lack of detectable trifluoromethylalcohols indicated quantitative oxidation.

There are additional approaches for preparing perfluoroalkyl ketones which involve the addition of perfluoroalkyl anions to suitable amino acid derivatives, such as addition of trifluoromethyl zinc to amino acid aldehydes and addition of pentafluoroethyl lithium to protected amino acid esters (R. Cregge et al., *J. Fluorine Chem.*, 88, 71 (1998)).

D. Chloromethyl Ketone-Based Libraries

Peptide chloromethylketones are traditionally synthesized by coupling a carboxylic acid to diazomethane using an isobutylchloroformate mixed anhydride procedure, followed by treatment with HCl (FIG. 8) (Schoellmann & Shaw, *Biochem.*, 2, 252 (1963); Green & Shaw, *J. Biol. Chem.*, 256, 1923 (1981)). Coupling can be accomplished for solid phase chloromethyl ketone synthesis using the HATU/TMP coupling method, or other coupling reagents. Conversion to the chloromethyl ketone on resin can be effected with dilute HCl in suitable solvents such as either, DCM, DMF, THF, etc.

Although chloromethyl ketones are unlikely to have clinical application, given their alkylating capability, they form covalent adducts with their targets and have a number of biochemical applications in the study of structure/function relationships in proteins. Chloromethyl ketones are also excellent synthetic intermediates for elaboration into a number of interesting peptide mimetic classes, such as hydroxyethylene inhibitors which are effective inhibitors of HIV protease (cf. Dreyer et al., *Biochem.*, 31, 6646 (1992); Knovalinka et al., *Eur. J. Biochem.*, 250, 559 (1997)), and the Alzheimer's disease-related 13-secretase enzyme (Shearman et al., *Biochem* 39, 8698 (2000)), among others.

E. Peptide Hydroxamic Acids

Peptide hydroxamic acids can be synthesized by coupling O-t-butyl hydroxylamine to the C-terminal carboxy group as the last step. The O-t-butyl protecting group is analogous to the t-butyl ester used to protect amino acids in this strategy, and is removed under acidic cleavage conditions. Peptide hydroxamic acids were synthesized based on the approach outlined in FIG. 9. Resin loaded with the Phe-Ala-Gly or Phe-Leu-Val was coupled with O-(t-butyl)hydroxylamine (HCl salt) using HATU/TMP, followed by cleavage with 10% TFMSA/TFA to give the corresponding hydroxamic acids. O-(t-butyl)hydroxylamine was found to give a better yield and purity of the final peptide hydroxamic acid than the use of unprotected hydroxylamine.

The cleaved peptide trifluoromethylketones, peptide boronic acids, and peptide hydroxamic acids were obtained in high purity (>70% in HPLC). HPLC purity and molecular weight confirmation of the peptides/peptide mimetics are given in Table 4.

EXAMPLE 6

Two additional strategies for the solid phase attachment of nascent peptide chains to the solid phase have been developed. These strategies allow inverse peptide synthesis of a peptide chain to be performed using the present t-butyl ester based inverse peptide synthesis method, followed by chemical cleavage from the resin. In Examples 1-2 above, the product peptide always has a succinyl, Glu or Gln residue as its N-terminus. Two other attachment strategies have been developed for use in the present t-butyl ester based inverse peptide synthesis method, which permit the synthesis of peptides/mimetics with virtually any N-terminal substituents, including free $NH_2$.

A. Dde Attachment Strategy

Figure 10:
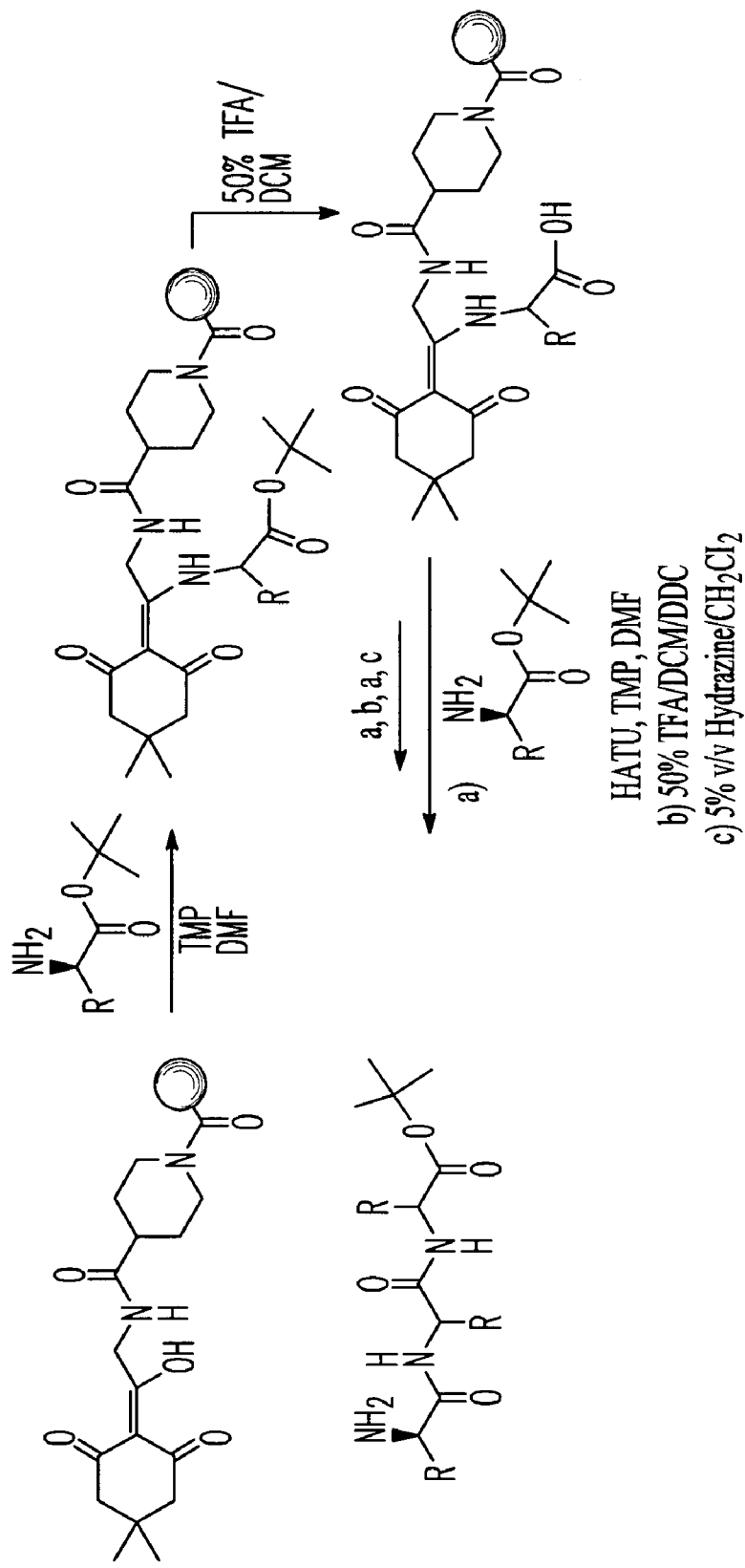
FIG. 10 depicts a Dde resin based inverse peptide synthesis.

Dde resin is commercially available and has been described in the literature (S. R. Chhabra et al., *Tetrahedron Lett.*, 41, 1095 (2000)). The Dde functional group reacts with amines as shown in FIG. 10. After reactions on the Dde-amine conjugate the amine can be released by treatment with hydrazine, and the peptide deprotected.

Using commercially available Dde resin from Novabiochem, an amino acid t-butyl ester can be attached to the resin simply by incubating the amino acid ester with the resin in the presence of a suitable base. The present t-butyl ester based inverse peptide synthesis cycles can then be used to elaborate a peptide chain on the resin. The t-butyl C-terminal carboxyl protecting group can be removed before cleavage from the resin, or left intact if a carboxy group protected peptide is desired. Cleavage of the peptide product using hydrazine provides a side chain and optionally, a carboxy group-protected peptide/mimetic with a free N-terminal amine (Step (c)).

Treatment of these peptides/mimetics off-resin with TFMSA/TFA, as shown in FIG. 11, provides the side chain- and carboxy group-deprotected peptide. Several side chain and C-terminally protected and deprotected peptides were synthesized using this method in good yield and purity. Analysis of product peptides for racemization using Marfey's reagent as cited above revealed <3% racemization at all residues. A trifluoromethyl ketone synthesis from the trifluoromethyl amino alcohol has been successful with this strategy, demonstrating that this attachment strategy is stable to on resin oxidation. (See Example 4(C).)

1. Materials

Dde resin (R-Dde) (0.87 mmole/g, 100-200 mesh) was purchased from Calbiochem-Novabiochem AG (Switzerland), and amino acid t-butyl esters were purchased from Bachem AG (King of Prussia, Pa.). HATU (0-(7-azabenzotriazol-1-yl)-N,N,N',N'-tetramethyluronium hexafluorophosphate), TMP (2,4,6-trimethylpyridine), anhydrous NMP (N-methylpyrrolidone), TFA (trifluoroacetic acid), TFMSA (trifluoromethanesulfonic acid), and hydrazine were from Aldrich (Milwaukee, Wis., USA). Anhydrous DMF (N,N-dimethylformamide), and DCM (dichloromethane) were from Acros (N.J., USA). Marfey's Reagent (N$^\alpha$-(2,4-dinitro-5-fluorophenyl)-L-alaninamide) was from Sigma (St. Louis, Mo., USA).

2. Methods a. Loading of the First Amino Acid

The overall synthesis strategy is outlined in FIG. 10. To load the first amino acid, Dde resin (R-Dde) was swollen in DMF for 2 hours and then washed with DMF. To the resin was added a freshly prepared solution of an amino acid t-butyl ester (AA-OtBu•HCl) (5 eq) and TMP (10 eq) in DMF, and mixed for 2 hours. The resin was filtered and washed with DMF, and another solution of freshly prepared AA-OtBu•HCl (5 eq) and TMP (10 eq) in DMF was again added to the resin and mixed for 12 hours. The resin was then washed and dried.

b. Inverse Peptide Synthesis

Inverse peptide synthesis cycles performed as summarized in Table 2, using an HATU/TMP based coupling method (A. Johansson et al., *J. Comb. Chem.*, 2, 496 (2000); W. G. Gutheil et al., *Chem. Pharm. Bull.* (Tokyo), 50, 688 (2002)).

c. Cleavage of Peptides from Resin

Peptide-resin samples (10 mg) were treated with 5% hydrazine/DCM (400 μl) for 60 min. The cleavage solution was filtered, dried, and analyzed by HPLC and LC/MS.

d. Side Chain Deprotection

Off-resin treatment of a protected peptide Tyr-Ala-Val-Lys (Z)-OtBu (SEQ ID NO:5) with 10% TFMSA/TFA for 30 minutes was used to quantitatively deprotect peptide to give H$_2$N-Tyr-Ala-Val-Lys-OH (SEQ ID NO:5) (Scheme 3).

e. HPLC

HPLC was performed on a Hewlett-Packard series 1050 system equipped with a diode array detector and a C18 column (Solvent miser, 2.1×250 nm, 5.0 μm particles). Compounds were separated by gradient elution; 100% solvent A (0.1% TFA in water) for 1 min, then 0% to 100% of solvent B (0.1% TFA in 30:70 water:acetonitrile) in 10 min, and then 0% to 100% of solvent C (0.095% TFA in acetonitrile) in 5 min. LC/MS was carried out on ThermoQuest (Finnigan) system equipped with atmospheric-pressure ionization (API) electro spray source.

f. Determination of Racemization by Marfey's Reagent

The degree of racemization of amino acids in product peptides was determined using Marfey's reagent. A 2 μL aliquot of a 50 mM solution of peptide was hydrolyzed with 100 μL 6 N HCl for 4 hours at 110° C. in sealed vials, and the hydrolyzed mixture dried under vacuum. To this was added 14.3 μL (5 eq) of a 1% solution of Marfey's reagent in acetone, 4 μL of 1 M NaHCO$_3$ and 6 μL of water per amino acid, and the mixture was kept at 35-40° C. for 90 min. The reaction was quenched by the addition of 4 μL of 1 M HCl (per amino acid). Solvent was removed under vacuum and the residue dissolved in 400 μL of 1:1 water:acetonitrile. A 10 μL injection was made for HPLC analysis (detection at 340 nm). The same procedure except for hydrolysis was followed for standards (50 mM solution of amino acids). The percentage of D-diastereomer for each amino acid in each hydrolyzed sample determined by comparison of peak areas.

3. Solid-Phase Synthesis of Two Peptide Trifluoromethylketones; Tyr-Ala-Val-NHCH(CH$_3$)C(O)CF$_3$ and Gly-Val-NHCH(CH$_3$)C(O)CF$_3$ To demonstrate the potential of the Dde resin based attachment strategy for peptide mimetic syntheses, two peptide trifluoromethylketones were synthesized based on the approach outlined in FIG. 12. R-Dde-Tyr-Ala-Val and R-Dde-Gly-Val were subjected to HATU/TMP coupling with racemic 1-trifluoromethyl-2-amino-1-propanol (HCl.NH$_2$CH(CH$_3$)CH(OH)CF$_3$) in DMF for 6 hours (B. Imperiali et al., *Tetrahedron Lett.*, 27, 135 (1986)). This procedure was repeated once, and the resins washed and dried to provide R-Dde-Tyr-Ala-Val-NHCH(CH$_3$)CH(OH)CF$_3$ and R-Dde-Gly-Val-NHCH(CH$_3$)CH(OH)CF$_3$. R-Dde-Tyr-Ala-Val-NHCH(CH$_3$)CH(OH)CF$_3$ and R-Dde-Gly-Val-NHCH(CH$_3$)CH(OH)CF$_3$ were treated with a solution of DCC/CHCl$_2$COOH/DMSO/toluene (10 eq/1 eq/0.2 ml/0.2 ml) for 18 hours. After filtration and washing this procedure was repeated once. After filtration, washing, and drying the resins were treated with 400 μl 5% hydrazine/DCM for 60 min. The cleavage solution was filtered, dried and analyzed by HPLC and LC/MS.

4. Results

Seven short peptides were synthesized using this strategy and analyzed for degree of amino acid racemization using Marfey's reagent. The degree of racemization was less than 3% in all cases. All seven peptides were obtained in good yields and purity (Table 6).

TABLE 6

Purity and yields of peptides and peptide mimetics

| | Peptide/Peptide Mimetic | Purity[a] (%) | Purity[b] (%) |
|---|---|---|---|
| 1 | Tyr-Ala-Val-OtBu | 95 | >85 |
| 2 | Gly-Pro-Leu-OtBu | 95 | >85 |

TABLE 6-continued

Purity and yields of peptides and peptide mimetics

| | Peptide/Peptide Mimetic | Purity[a] (%) | Purity[b] (%) |
|---|---|---|---|
| 3 | Phe-Gly-Val-OtBu | 85 | >80 |
| 4 | Tyr-Ala-Leu-OtBu | 80 | >75 |
| 5 | Tyr-Gly-Orn(Z)-OtBu | 80 | >70 |
| 6 | Ala-Lys(Z)-Gly-OtBu | 95 | >85 |
| 7a | Tyr-Ala-Val-Lys(Z)-OtBu (SEQ ID NO: 5) | 90 | >75 |
| 7b | Tyr-Ala-Val-Lys-OH (SEQ ID NO: 5) | 95 | >95[c] |
| 8 | Tyr-Ala-Val-NHCH(CH$_3$)COCF$_3$•H$_2$O | 85 | >80 |
| 9 | Gly-Val-NHCH(CH$_3$)COCF$_3$•H$_2$O | 85 | >80 |

[a]Determined by HPLC of cleaved peptide/peptide mimetic.
[b]Determined by amount of peptide obtained after cleavage.
[c]From 7a.

Off-resin treatment of a protected peptide with 10% TFMSA/TFA for 30 minutes can be used to quantitatively deprotect peptide, as demonstrated by off-resin treatment of Tyr-Ala-Val-Lys(Z)-OtBu (SEQ ID NO:5) to give Tyr-Ala-Val-Lys-OH (FIG. 12, Table 6 entry 7b (SEQ ID NO:5)). An effort to perform side chain deprotection on-resin gave a complex mixture of products.

Fluoromethylketones are of interest as inhibitors of serine, cysteine, and aspartic acid proteases, including elastase, Cathepsin B, renin, and HIV protease. To demonstrate the potential of the Dde resin based attachment strategy for peptide mimetic syntheses, two peptide trifluoromethylketones were synthesized. R-Dde-Tyr-Ala-Val and R-Dde-Gly-Val were coupled with an aminotrifluoromethylalcohol to give the corresponding resin attached peptide trifluoromethylalcohols. Oxidation of the alcohol by Pfitzner-Moffat oxidation gave the corresponding resin attached peptide trifloromethylketones. After cleavage the peptide trifluoromethylketones were obtained in good yield and high purity. In LC/MS they were detected as their hydrates. The lack of detectable peptide trifluoromethylalcohol indicated quantitative oxidation.

C. Backbone Attachment Strategy (Backbone Amide Linker-BAL Strategy)

As discussed and referenced above, a number of studies demonstrate that amines and amino acid esters can be attached to a solid support via a benzylic attachment. These attached amines are amenable to elaboration by suitable synthetic methods, followed by cleavage from the solid support to give the desired products. Further recent studies demonstrate that an attached amino acid can be extended by normal (N-to-C) peptide synthesis cycles, with the peptide chain anchored through the backbone amide of the C-terminal residue (Backbone Amide Linker strategy (BAL)). See FIG. 14. This allows an attached peptide to be synthesized in the classic C-to-N direction, with the free C-terminus available for elaboration into suitable peptide mimetic functional groups, and provides an alternative to the inverse (N-to-C) synthesis strategy.

However, the normal direction BAL strategy suffers from several limitations—primarily from the limitation that the peptide chain is synthesized in the C-to-N direction, away from the C-terminal functional group. For split-pool combinatorial peptide mimetic synthesis followed by iterative deconvolution to obtain an optimized agent(s), which is arguably one of the better approaches to combinatorial optimization (D. A. Konings et al., *J. Med. Chem.*, 40, 4386 (1997)), it is the last residues added to a molecule which are optimized first. In the BAL approach with C-to-N synthesis cycles these are the residues furthest away from the C-terminal functional group. It seems most reasonable when optimizing a C-terminal peptide mimetic for a specific application to optimize the residues closest to the C-terminus first. By combining the BAL attachment strategy with t-butyl ester based inverse peptide synthesis would provide a method for the synthesis of C-terminally modified peptides comprising a wide variety of capping groups at the N-terminus, including various N-terminal capping groups such as acyl, ureido, sulfamoyl, etc., as well as cyclic peptides and the like.

Figure 13:
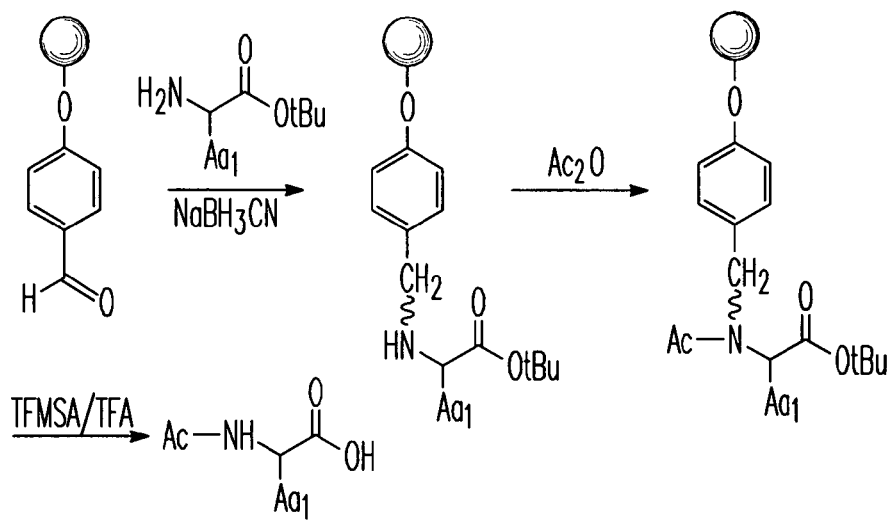
FIG. 13 depicts a backbone synthesis strategy using an aldehyde resin wherein (•) represents the resin matrix.

Two phenoxybenzaldehyde resins for BAL attachment have been found suitable for amino acid t-butyl ester based ISPPS (commercially available from NovaBiochem), a mono-methoxy benzaldehyde resin (MM, above), and a no-methoxy benzaldehyde resin (NM, above). As shown in FIG. 13, an amino acid t-butyl ester is loaded onto the benzaldehyde resins by reductive amination. Treatment with acetic anhydride/DIPEA caps the secondary amine easily as an acetyl derivative on the monomethoxy resin, but capping is more difficult on the no-methoxy resin, and more stringent conditions are often required such as the use of acyl fluorides as has been observed in other studies of acylation of benzylically attached amines (G. T. Bourne et al., *J. Org. Chem.*, 64, 3095 (1999)). In principle, a wide variety of acyl groups can be used to cap the secondary amine, including N-protected amino acids, acyl groups, ureido groups, and sulfonyl groups, etc., and this can potentially be used to provide a great variety of diversity in peptides/mimetics accessible with this approach. After loading and acylation the peptide chain can be extended in the inverse direction using the tBu ester approach.

For t-butyl ester based ISPPS reactions on the monomethoxy resin, poor yields of the product peptides were observed when 50% TFA/CH$_2$Cl$_2$ was used in the deprotection reaction, and resin fragments were also present in the peptide products. A study was therefore made of yield and purity of a model tripeptide (Ac-Phe-Ala-Val) as a function of % TFA in the TFA/CH$_2$Cl$_2$ deprotection reagent, with the results summarized in Table 7. Excellent results were obtained in a window of from 20-30% TFA. At lower % TFA than 20%, incomplete deprotection of tBu esters resulted in deletion peptides, whereas at higher than 30% TFA in deprotection reactions, the resin attachment is prematurely cleaved resulting in decreased yields of the final product, and the optimal % TFA for OtBu deprotection on the monomethoxy resin based on this study is 25%. The acid stability of the attachment to the no-methoxy resin is higher than for the mono-methoxy resin, and 50% TFA can be used with the no-methoxy resin without adverse consequences.

TABLE 7

Effect of % TFA in OtBu deprotection reagent on product purity
and yield for ISPPS on monomethoxy phenoxy benzaldehyde resin.

| % TFA/DCM | Resin Fragments | Purity Ac-Phe-Ala-Val[a] | Total Recovery Phe containing peptides | % Yield Ac-Phe-Ala-Val |
|---|---|---|---|---|
| 5% | – | 40% | >95% | 52% |
| 10% | – | 44% | >95% | 58% |
| 15% | – | 58% | >95% | 69% |
| 20% | – | >95% | >95% | 88% |
| 25% | – | >95% | >95% | 92% |
| 30% | – | >95% | >95% | 94% |
| 40% | + | >95% | 73% | 69% |
| 50% | ++ | >95% | 62% | 60% |

[a]Compared to all Phe containing peptides (eg. not including resin fragments).

For both mono and no-methoxy resins, peptide is released from the resin with 10% TFMSA/TFA. Other standard cleavage methods for Boc chemistry compatible attachment strategies are also expected to work for releasing product peptides for both mono- and no-methoxy resin based backbone attachment strategies, such as 95% TFA/$H_2O$ and HF.

These examples demonstrate that irreversible capping reactions of the backbone linked secondary amine with acyl (acetyl) groups provide the acyl capped peptide product after cleavage from the resin. In contrast, urethane (Fmoc and Cl-Cbz) groups were cleaved from the peptides during cleavage of the peptides from the resin. It is expected that essentially all acyl groups will provide irreversible capping groups, whereas all urethanes will provide cleavable capping groups.

It is desirable to have several different irreversible capping groups to provide additional diversity in product peptide mimetics for screening. Benzenesulfonyl groups are one such capping group of interest. In preliminary studies it has been observed that use of a sulfonyl capping group on the monomethoxy resin leads to a resin attachment linkage which is unstable to TFA deprotection conditions for inverse peptide synthesis. It is expected that a no-methoxy substituted resin will be more stable, and will allow peptides with a sulfonyl capping group to be synthesized. Another capping group of interest are ureas, which can be introduced by treating the secondary amine after loading the first amino acid with an isocyanate.

Figure 16:
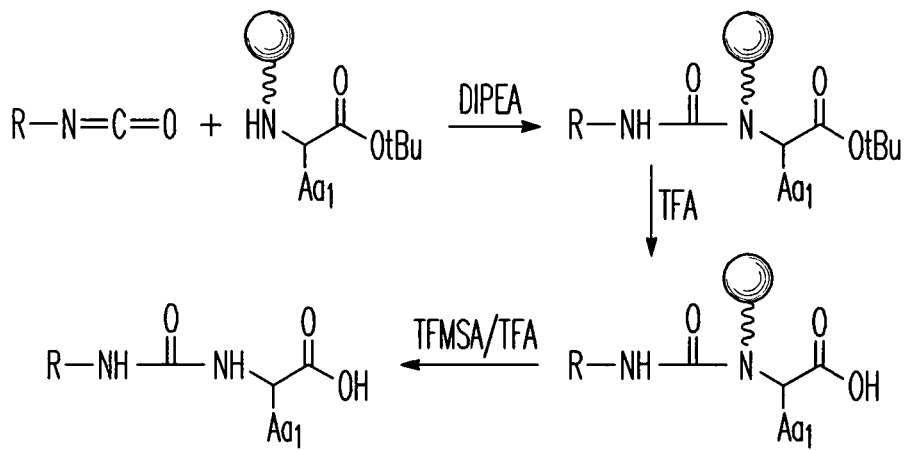
FIG. 16 depicts a urea capping reaction.

For N-terminal capping with substituted urea groups, the resin loaded with the first residue (L-Phe) will be treated with a ten molar excess (10×) of benzylisocyanate in the presence of DIPEA overnight in DMF, and then washed and dried. The resin will be tested for the absence of secondary amino groups with the chloranil test and for the absence of carboxyl groups with the Malachite Green test. The resin will be treated with TFA to deprotect the t-butyl ester, and the resin tested for the absence of secondary amine and the presence of carboxyl group. The product BzNHCO—NH-Phe will be cleaved from the resin, and yield, identity, and purity determined by HPLC and LC/MS (FIG. 16). A series of tripeptide ureas will be made with several isocyanates and amino acids to determine the scope and generality of this method.

Figure 15:
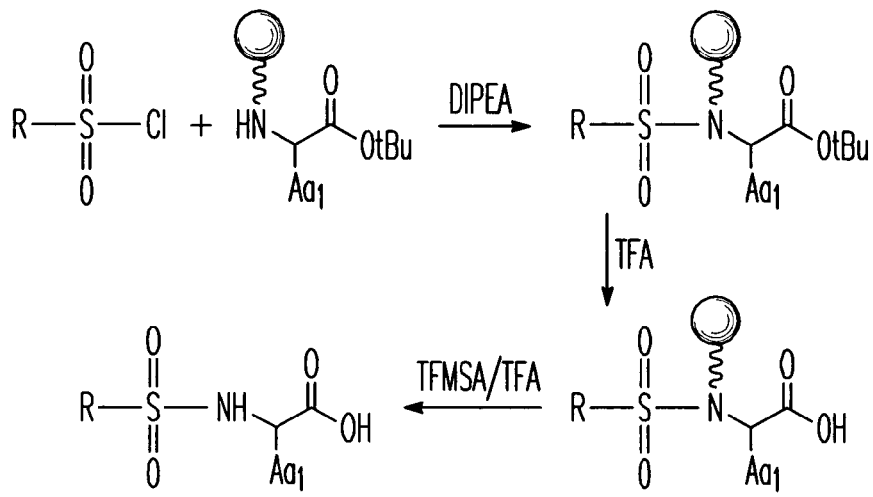
FIG. 15 depicts a sulfamoyl capping reaction.

For N-terminal capping with substituted sulfamoyl groups, a similar strategy to that described for peptide ureas will be followed (FIG. 15). Preliminary studies on a mono-methoxy resin demonstrate that a sulfamoylated secondary amine linkage is unstable to TFA, so it is proposed to test the more acid stable no-methoxy resin in this application. Preliminary studies will use benzene sulfonyl chloride as the sulfamoylating agent. A series of sulfamoylating agents will be used to synthesize a series of peptide sulfonamides to determine the scope and generality of this method.

All cited publications, patent applications, and patents are incorporated by reference herein as though fully set forth.

What is claimed is:

1. A method of preparing an immobilized peptide derivative of formula (Vb):

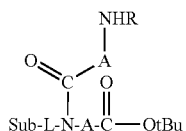

(Vb)

comprising:

(a) reacting a functionalized solid support of general formula Sub(L)X, wherein Sub is a solid support, L is a cleavable linker, and X is a leaving group, wherein (L)X comprises a group of formula

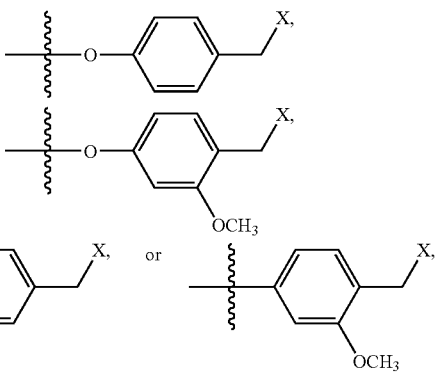

wherein a bond bisected by a wavy line indicates a bond connecting L to Sub, with a compound of formula:

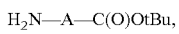

wherein tBu is a tert-butyl group, and wherein the N—A—C(O) group is a residue of an amino acid or of a peptide composed of independently selected amino acid residues, to yield an immobilized peptide derivative of formula:

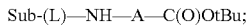

then, (b) contacting the immobilized peptide derivative of the formula:

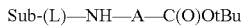

with compound of the formula RHN—A—C(O)OH, wherein the RHN—A—C(O) group is the residue of a N-protected α-amino acid, in the presence of a coupling agent, to yield an immobilized peptide derivative of the formula (Vb):

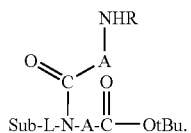
(Vb)

2. The method of claim 1, further comprising removing the tBu group from the immobilized peptide derivative of formula (Vb) to provide the immobilized peptide derivative of formula (Va):

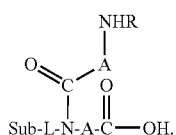
(Va)

3. The method of claim 1, further comprising N-deprotecting the immobilized peptide derivative of formula (Vb) by removal of R, then acylating with an N-protected peptide in the presence of a coupling agent, to provide an N-terminal blocked immobilized peptide derivative of formula (VIII):

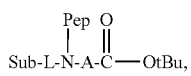
(VIII)

wherein Pep is an N-protected peptide residue.

4. The method of claim 2, further comprising contacting the immobilized peptide derivative of formula (Va) with an amino ester or peptide ester derivative of formula (III):

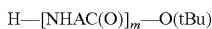
(III), wherein m is a positive integer, and wherein each N—A—C(O) group is independently a residue of an amino acid or a peptide residue composed of independently selected amino acid residues, in the presence of a coupling agent, to yield an immobilized peptide derivative of formula (XXI):

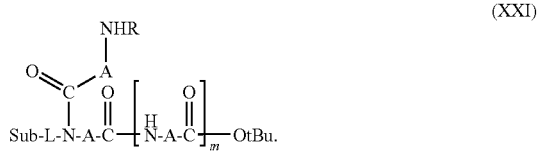
(XXI)

5. The method of claim 4 further comprising removing the tBu group from the immobilized peptide derivative of formula (XXI) to provide an immobilized peptide derivative of formula (XXIa):

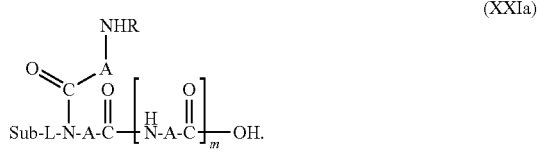
(XXIa)

6. The method of claim 5 further comprising preparation of a peptide derivative of formula (XXIb):

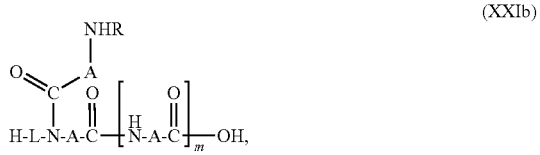
(XXIb)

comprising cleaving the immobilized peptide derivative (XXIa) at the [L]—N bond.

7. The method of claim 3, further comprising removing the tBu group from the immobilized peptide derivative of the formula (VIII) to provide the N-terminal blocked immobilized peptide derivative of formula (VIIIa):

(VIIIa)

8. The method of claim 7, further comprising contacting the compound of formula (VIIIa) with an amino ester or peptide ester derivative of formula (III):

(III), wherein m is a positive integer and wherein the N—A—C(O) group is a residue of an amino acid or a peptide residue composed of independently selected amino acid residues, in the presence of a coupling agent, to yield an N-terminal blocked immobilized peptide derivative of formula (VIIIb):

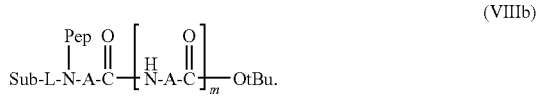
(VIIIb)

9. The method of claim 8, further comprising removing the tBu group from the immobilized peptide derivative of the formula (VIIIb) to provide an N-terminal blocked immobilized peptide derivative of formula (VIIIc):

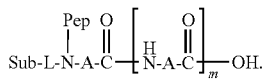
(VIIIc)

10. The method of claim 9, further comprising preparation of an N-terminal blocked peptide derivative of formula (VIIId):

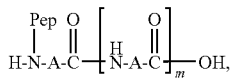
(VIIId)

comprising cleaving the immobilized peptide derivative (VIIIc) at the [L]—N bond.

11. The method of claim 7, further comprising preparation of an N-terminal blocked peptide derivative of formula (VIIIe):

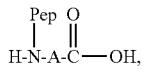
(VIIIe)

comprising cleaving the immobilized peptide derivative (VIIIa) at the [L]—N bond.

12. The method of claim 2 further comprising preparation of a peptide derivative of formula (IXa);

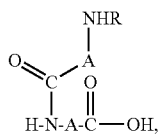
(IXa)

comprising cleaving compound (Va) at the L—N bond.

13. The method of claim 1 wherein [L]X is

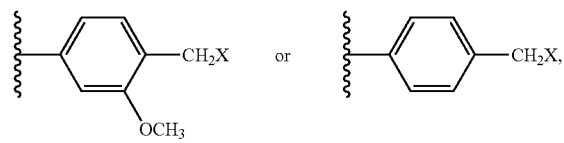

and
wherein X is halo, tosyl or mesyl, and wherein a bond bisected by a wavy line indicates a bond connecting L to Sub.

14. A method of preparing an immobilized peptide derivative of the formula

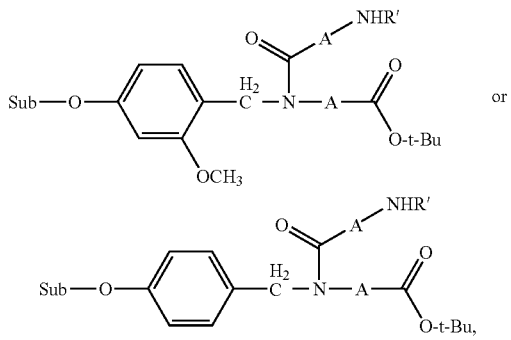

comprising:
(a) reacting a functionalized solid support of formula

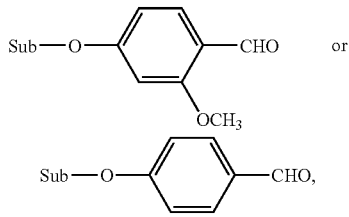

wherein Sub is a solid support,
with H—[NH—A—C(O)]—O(tBu), wherein tBu is a tert-butyl group, and wherein the N—A—C(O) group is a residue of an amino acid or of a peptide composed of independently selected amino acid residues, under conditions of reductive amination to yield a respective immobilized compound of the formula

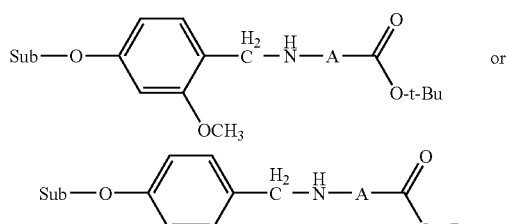

then,
(b) contacting the immobilized compound of the formula

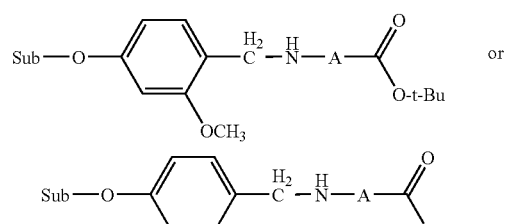

with a compound of the formula R'HN—A—C(O)OH, wherein the R'HN—A—C(O) group is the residue of a N-protected α-amino acid, in the presence of a coupling agent, to yield the immobilized peptide derivative of the respective formula

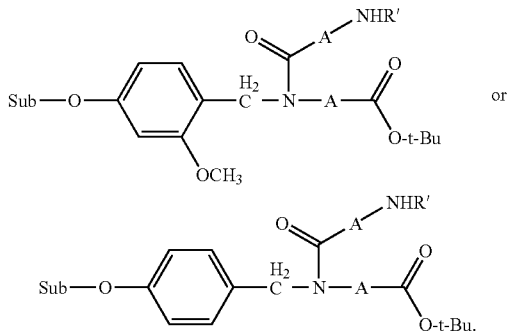

or

15. The method of claim 1 wherein N—A—C(O) is individually the residue of an α-amino acid optionally including a sidechain protecting group.

16. The method of claim 1 wherein N—A—C(O) is individually the residue of a naturally occurring L-amino acid optionally including a sidechain protecting group.

17. The method of claim 1 wherein the coupling agent comprises HATU.

18. The method of claim 2 wherein the tBu group is removed with a mixture comprising TFA and $CH_2Cl_2$.

19. The method of claim 6 wherein the step of cleaving at the L—N bond is carried out using a reagent system comprising TFMSA/TFA or hydrazine/DMF.

20. The method of claim 1 wherein Sub comprises an organic polymer.

21. The method of claim 2, further comprising contacting the immobilized peptide derivative of formula (Va), with $H_2N$—A—CH(OH)$CF_3$ (XV), wherein $H_2N$—A—CH(OH)$CF_3$ is a trifluoromethyl amino-carbinol, in the presence of a coupling agent, to yield by a dehydration reaction an immobilized peptide derivative comprising a C-terminal trifluoromethylcarbinol amide group of formula —NH—A—CH(OH)$CF_3$ wherein the —NH is bonded as an amide to a C-terminal carbonyl group of the immobilized peptide derivative.

22. The method of claim 21 wherein the coupling agent comprises HATU.

23. The method of claim 21, further comprising oxidizing the C-terminal trifluoromethylcarbinol amide group of formula —NH—A—CH(OH)$CF_3$ wherein the —NH is bonded as an amide to a C-terminal carbonyl group of the immobilized peptide derivative of formula (Va), to a trifluoromethylketone amide group of formula —NH—A—C(O)$CF_3$ wherein the —NH is bonded as an amide to a C-terminal carbonyl group of the immobilized peptide derivative.

24. The method of claim 23 wherein oxidizing the C-terminal trifluoromethylcarbinol is carried out using $KMnO_4$ Dess-Martin periodinane, or Pfitzer-Moffat reagent.

25. The method of claim 23, further comprising cleaving the L—N bond of the immobilized peptide derivative of formula (Va), having a C-terminal trifluoromethylketone amide group of formula —NH—A—C(O)$CF_3$ wherein the —NH is bonded as an amide to a C-terminal carbonyl group of the immobilized peptide derivative, to provide a peptide derivative of formula (IXa), having a C-terminal trifluoromethylketone amide group of formula —NH—A—C(O)$CF_3$ wherein the —NH is bonded as an amide to a C-terminal carbonyl group of the peptide derivative.

26. The method of claim 25, wherein cleaving the L—N bond is carried out using a reagent system comprising TFMSA/TFA or hydrazine/DMF.

27. The method of claim 21, further comprising cleaving the L—N bond of the immobilized peptide derivative of formula (Va), having a C-terminal trifluoromethylcarbinol amide group of formula —NH—A—CH(OH)$CF_3$ wherein the —NH is bonded as an amide to a C-terminal carbonyl group of the immobilized peptide derivative of formula (Va) to provide a peptide derivative of formula (IXa), having a C-terminal trifluoromethylcarbinol amide group of formula —NH—A—CH(OH)$CF_3$ wherein the —NH is bonded as an amide to a C-terminal carbonyl group of the peptide derivative.

28. The method of claim 27 wherein cleaving the L—N bond is carried out using TFMSA/TFA or hydrazine/DMF.

29. The method of claim 2, further comprising contacting the immobilized peptide derivative of formula (Va), with an optionally O-protected aminoboronic acid of the formula $H_2N(A)B(OR^4)_2$, wherein each $R^4$ is individually H, ($C_1$-$C_6$) alkyl, phenyl, or wherein $R^4$ is an alkyl diradical bonded to both boronate oxy groups, in the presence of a coupling agent, to provide an immobilized peptide derivative of formula (Va), further comprising a C-terminal —NH(A)B(OR$^4$)$_2$ group, wherein the —NH is bonded as an amide to a C-terminal carbonyl group of the immobilized peptide derivative.

30. The method of claim 29 wherein the coupling agent comprises HATU.

31. The method of claim 29 further comprising cleaving the L—N bond of the immobilized peptide derivative of formula (Va), further comprising a C-terminal —NH(A)B(OR$^4$)$_2$ group, wherein the —NH is bonded as an amide to a C-terminal carbonyl group of the immobilized peptide derivative, to provide a peptide derivative of formula (IXa), having a C-terminal —NH(A)B(OR$^4$)$_2$ group, wherein the —NH is bonded as an amide to a C-terminal carbonyl group of the peptide derivative.

32. The method of claim 31 wherein cleaving the L—N bond is carried out using TFMSA/TFA or hydrazine/DMF.

33. The method of claim 2, further comprising contacting the immobilized peptide derivative of formula (Va), with $H_2N(alkyl)OR^3$ wherein $R^3$ is H or a hydroxyl-protecting group, in the presence of a coupling agent, to provide an immobilized peptide derivative of formula (Va), further comprising a C-terminal —NH(alkyl)OR$^3$ group, wherein the —NH is bonded as an amide to a C-terminal carbonyl group of the immobilized peptide derivative.

34. The method of claim 33 wherein the coupling agent comprises HATU.

35. The method of claim 33 further comprising cleaving the L—N bond of the immobilized peptide derivative of formulas (Va), further comprising a C-terminal —NH(alkyl)OR$^3$ group, wherein the —NH is bonded as an amide to a C-terminal carbonyl group of the immobilized peptide derivative, to provide a peptide derivative of formula (IXa), having a C-terminal —NH(alkyl)OR$^3$ group, wherein the —NH is bonded as an amide to a C-terminal carbonyl group of the peptide derivative.

36. The method of claim 35 wherein cleaving the L—N bond is carried out using TFMSA/TFA or hydrazine/DMF.

* * * * *

UNITED STATES PATENT AND TRADEMARK OFFICE
CERTIFICATE OF CORRECTION

| | | |
|---|---|---|
| PATENT NO. | : 7,786,259 B2 | Page 1 of 1 |
| APPLICATION NO. | : 11/777899 | |
| DATED | : August 31, 2010 | |
| INVENTOR(S) | : William G. Gutheil | |

It is certified that error appears in the above-identified patent and that said Letters Patent is hereby corrected as shown below:

In the Claims, Claim 6,
Column 28, Lines 30-35,

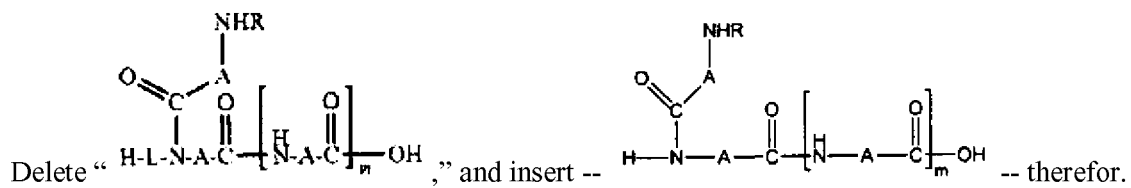

Claim 8,
Column 28, Line 53,
Delete "H—[NH—a—C(O)]$_m$—O(tBu)" and insert -- H-[NH-A-C(O)]$_m$-O(tBu) -- therefor.

Signed and Sealed this
Eighth Day of March, 2011

David J. Kappos
*Director of the United States Patent and Trademark Office*